(12) United States Patent
Peri et al.

(10) Patent No.: US 7,538,185 B2
(45) Date of Patent: May 26, 2009

(54) GLUCAGON-LIKE PEPTIDE-1 ANALOGS WITH LONG DURATION OF ACTION

(75) Inventors: Krishna Peri, St-Laurent (CA); Daniel Abran, Vaudreuil (CA); Abdelkrim Habi, Pierre Fonds (CA)

(73) Assignee: Theratechnologies Inc., Saint-Laurent, Quebec (CA)

( * ) Notice: Subject to any disclaimer, the term of this patent is extended or adjusted under 35 U.S.C. 154(b) by 161 days.

(21) Appl. No.: 11/031,851

(22) Filed: Jan. 7, 2005

(65) Prior Publication Data

US 2006/0014685 A1 Jan. 19, 2006

Related U.S. Application Data

(60) Provisional application No. 60/534,682, filed on Jan. 8, 2004, provisional application No. 60/570,073, filed on May 12, 2004.

(51) Int. Cl.
*A61K 38/26* (2006.01)
(52) U.S. Cl. .................. 530/308; 514/12; 530/324
(58) Field of Classification Search ............ 514/12; 530/308, 329, 324
See application file for complete search history.

(56) References Cited

U.S. PATENT DOCUMENTS 6,903,186 B1 * 6/2005 Dong .................... 530/324
7,067,488 B2 * 6/2006 Gravel et al. .................. 514/12

FOREIGN PATENT DOCUMENTS

| | | |
|---|---|---|
| CA | 2468374 | 3/1998 |
| CA | 2412004 | 12/2001 |
| CA | 2455963 | 2/2003 |
| CA | 2468700 | 7/2003 |
| EP | 1 359 159 | 11/2003 |
| WO | WO 91/11457 | 8/1991 |
| WO | WO 93/25579 | 12/1993 |
| WO | WO 98/19698 | 5/1998 |
| WO | WO 98/43658 | 10/1998 |
| WO | WO 99/43705 | 9/1999 |
| WO | WO 99/43706 | 9/1999 |
| WO | 00-37615 * | 6/2000 |
| WO | WO 00/34331 | 6/2000 |
| WO | WO 00/34332 | 6/2000 |
| WO | WO 01/98331 | 12/2001 |
| WO | WO 02/47716 | 6/2002 |
| WO | WO 03/018516 | 3/2003 |

OTHER PUBLICATIONS

Deacon et al., "Dipeptidyl peptidase IV resistant analogues of glucagon-like peptide-1 which have extended metabolic stability and improved biological activity," *Diabetologia*, 41:271-278, 1998.
Green et al., "Novel dipeptidyl peptidase IV resistance analogues of glucagon-like peptide-1(7-36)amide have preserved biological activities in vitro conferring improved glucose-lowering action in vivo," *J. Mol. Endocrin.*, 31:529-540, 2003.
Xiao et al., "Biological Activities of Glucagon-Like Peptide-1 Analogues in Vitro and in Vivo," *Biochemistry*, 40:2860-2869, 2001.
D'Alessio, D. et al., Diabetes, 1997, 46 (Suppl. 1) p. 29A.
Doyle, M.E. et al., Recent Prog. Horm. Res., 2001, 56, pp. 377-399.
Drucker, D.J., Endocrinology, 2001, 142 (2), pp. 521-527.
Drucker, D.J., Curr. Pharm. Des., 2001, 7 (14), pp. 1399-1412.
Gutniak, M. et al., 1992, New England Journal of Medicine, 1992, 326 (20), pp. 1316-1322.
Gutniak, M.K., Intl. Diabet. Monitor, 1997, 9 (2), pp. 1-12.
Holst, J.J., TEM, 1999, 10 (6), pp. 229-235.
Holst, J.J., Gastroenterology, 1994, 107, pp. 1848-1855.
Holz, G.G. et al., J. Biol. Chem., 1995, 270 (30), pp. 17749-17757.
Kieffer, T.J. et al., Endocrine Reviews, 1999, 20 (6), pp. 876-913.
Nauck, M.A. et al., Drug News Perspect, 2003, 16 (7), pp. 413-422.
Nauck, M.A., 1997, Current Opinion in Endocrinology and Diabetes, 1997, 4, pp. 291-299.
Nauck, M.A. et al., Diabetologia, 1996, 39, pp. 1546-1553.
Nauck, M.A. et al., Diabetologia, 1993, 36, pp. 741-744.
Nauck, M.A. et al., Diabetologia, 1986, 29, pp. 46-52.
Perfetti, R. et al., European Journal of Endocrinology, 2000, 143, pp. 717-725.
Scrocchi, L.A. et al., Nature Medicine, 1996, 2 (11), 1254-1258.
Todd, J.F. et al., Clinical Science, 1998, 95, pp. 325-329.
Toft-Nielsen, M.B. et al., Diabetes Care, 1999, 22 (7), pp. 1137-1143.
Tolessa, T. et al., J. Clin. Invest., 1998, 102 (4), pp. 764-774.
Vilsboll T. et al., J. Clinical Endocrinology & Metabolism, 2003, 88 (1), pp. 220-224.
Wang, Y. et al., J. of Clinical Investigation, 1997, 99 (12), pp. 2883-2889.
Xu, G. et al., Diabetes, 1999, 48, 2270-2276.

* cited by examiner

*Primary Examiner*—David Lukton
(74) *Attorney, Agent, or Firm*—Fulbright & Jaworski L.L.P.

(57) ABSTRACT

Novel GLP-1 analogs having improved biological potency as well as extended pharmacological activity are described herein. More specifically, the present invention relates to GLP-1 analogs (28 or 29 aa long) comprising amino acid substitutions at one or more of the following positions: 8, 20, 27, 30 and 33.

32 Claims, 18 Drawing Sheets

*P < 0.01

*P < 0.01 vs 20 mM acetic acid

*P < 0.01 vs Vehicle

*P<0.001 vs Vehicle

*p < 0.05 vs Vehicle using ANOVA

SEQUENCE LISTING

```
<160> NUMBER OF SEQ ID NOS: 23

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

His Gly Glu Gly Thr Phe Thr Ser Asp Val Ser Ser Tyr Leu Glu Gly
  1               5                  10                  15

Gln Ala Ala Lys Ala Phe Ile Glu Trp Leu Val Lys Asn
             20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

His Ala Glu Gly Thr Phe Thr Ser Asp Val Ser Ser Tyr Leu Glu Gly
  1               5                  10                  15

Gln Ala Ala Lys Leu Phe Ile Glu Trp Leu Lys Asn
             20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (29)
<223> OTHER INFORMATION: Aib

<400> SEQUENCE: 3

His Ala Glu Gly Thr Phe Thr Ser Asp Val Ser Ser Tyr Leu Glu Gly
  1               5                  10                  15

Gln Ala Ala Lys Ala Phe Ile Glu Trp Leu Lys Asn Xaa
             20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence:  Synthetic
      Peptide
```

<400> SEQUENCE: 4

His Gly Glu Gly Thr Phe Thr Ser Asp Val Ser Ser Tyr Leu Glu Gly
 1               5                  10                  15

Gln Ala Ala Lys Ala Phe Ile Glu Trp Leu Lys Asn
            20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

His Gly Glu Gly Thr Phe Thr Ser Asp Val Ser Ser Tyr Glu Gly Gln
 1               5                  10                  15

Ala Ala Lys Ala Phe Ile Glu Trp Leu Lys Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

His Ala Glu Gly Thr Phe Thr Ser Asp Val Ser Ser Tyr Leu Glu Gly
 1               5                  10                  15

Gln Ala Ala Lys Leu Phe Ile Glu Trp Leu Lys Asn
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

His Ala Glu Gly Thr Phe Thr Ser Asp Val Ser Ser Tyr Glu Gly Gln
 1               5                  10                  15

Ala Ala Lys Ala Phe Ile Glu Trp Leu Lys Asn
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

His Ala Glu Gly Thr Phe Thr Ser Asp Val Ser Ser Tyr Leu Glu Gly
 1               5                  10                  15

Gln Ala Ala Lys Leu Phe Ile Glu Trp Leu Val Lys Asn
            20                  25

```
<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

His Ala Glu Gly Thr Phe Thr Ser Asp Val Ser Ser Tyr Leu Glu Gly
  1               5                  10                  15

Gln Ala Ala Lys Ala Phe Ile Glu Trp Leu Lys Asn
             20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

His Ala Glu Gly Thr Phe Thr Ser Asp Val Ser Ser Tyr Leu Glu Gly
  1               5                  10                  15

Gln Ala Ala Lys Ala Phe Ile Glu Trp Leu Val Lys Asn
             20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

His Ala Glu Gly Thr Phe Thr Ser Asp Val Ser Ser Tyr Glu Gly Gln
  1               5                  10                  15

Ala Ala Lys Ala Phe Ile Glu Trp Leu Val Lys Asn
             20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

His Ala Glu Gly Thr Phe Thr Ser Asp Val Ser Ser Tyr Glu Gly Gln
  1               5                  10                  15

Ala Ala Lys Glu Phe Ile Ala Trp Leu Val Lys Gly Arg
             20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 13

His Gly Glu Gly Thr Phe Thr Ser Asp Val Ser Ser Tyr Glu Gly Gln
 1               5                  10                  15

Ala Ala Lys Glu Phe Ile Ala Trp Leu Val Lys Gly Arg
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

His Ala Glu Gly Thr Phe Thr Ser Asp Val Ser Ser Tyr Glu Gly Gln
 1               5                  10                  15

Ala Ala Lys Glu Phe Ile Ala Trp Leu Val Lys Gly Arg
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (28)
<223> OTHER INFORMATION: Aib

<400> SEQUENCE: 15

His Ala Glu Gly Thr Phe Thr Ser Asp Val Ser Ser Tyr Glu Gly Gln
 1               5                  10                  15

Ala Ala Lys Glu Phe Ile Ala Trp Leu Val Lys Xaa Arg
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 16

His Ala Glu Gly Thr Phe Thr Ser Asp Val Ser Ser Tyr Leu Glu Gly
 1               5                  10                  15

Gln Ala Ala Lys Leu Phe Ile Glu Trp Leu Lys Asn Gly
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 17

His Gly Glu Gly Thr Phe Thr Ser Asp Val Ser Ser Tyr Leu Glu Gly
 1               5                  10                  15

Gln Ala Ala Lys Leu Phe Ile Glu Trp Leu Lys Asn
            20                  25
```

```
<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

His Gly Glu Gly Thr Phe Thr Ser Asp Val Ser Ser Tyr Leu Glu Gly
  1               5                  10                  15

Gln Ala Ala Lys Leu Phe Ile Glu Trp Leu Val Lys Asn
             20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

His Ala Glu Gly Thr Phe Thr Ser Asp Val Ser Ser Tyr Glu Gly Gln
  1               5                  10                  15

Ala Ala Lys Leu Phe Ile Glu Trp Leu Lys Asn
             20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

His Ala Glu Gly Thr Phe Thr Ser Asp Val Ser Ser Tyr Glu Gly Gln
  1               5                  10                  15

Ala Ala Lys Leu Phe Ile Glu Trp Leu Val Lys Asn
             20                  25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

His Gly Glu Gly Thr Phe Thr Ser Asp Val Ser Ser Tyr Glu Gly Gln
  1               5                  10                  15

Ala Ala Lys Leu Phe Ile Glu Trp Leu Lys Asn
             20                  25

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide
```

-continued

```
<400> SEQUENCE: 22

His Gly Glu Gly Thr Phe Thr Ser Asp Val Ser Ser Leu Glu Gly Gln
1               5                   10                  15

Ala Ala Lys Ala Phe Ile Glu Trp Leu Lys Asn
            20                  25

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 23

His Ala Glu Gly Thr Phe Thr Ser Asp Val Ser Ser Tyr Glu Gly Gln
1               5                   10                  15

Ala Ala Lys Glu Phe Ile Ala Trp Leu Val Lys Gly Arg
            20                  25
```

GLUCAGON-LIKE PEPTIDE-1 ANALOGS WITH LONG DURATION OF ACTION

CROSS REFERENCE TO RELATED APPLICATIONS

This application claims the benefit of U.S. Provisional Applications No. 60/534,682 and 60/570,073, filed Jan. 8, 2004 and May 12, 2004 respectively, of which the entire text is incorporated by reference.

FIELD OF THE INVENTION

The present invention relates to glucagon-like peptide-1 analogs. Moreover, the present invention relates to glucagon-like peptide-1 analogs with long duration of action.

BACKGROUND OF THE INVENTION

Oral ingestion of food leads to the secretion of insulin and insulin counter regulatory hormones in a concerted effort to control blood glucose levels by increasing glucose and free fatty acid uptake by liver, muscle and adipose tissue, and by reducing gluconeogenesis from the liver. Insulin secretion is modulated by secretagogue hormones, termed incretins, produced by enteroendocrine cells. Glucose-dependent Insulinotropic Peptide (GIP) and Glucagon-Like Peptide-1 (GLP-1) account for almost all of the incretin effect. In contrast to GIP, GLP-1 is effective in diabetic subjects. Thus, there is a great deal of interest in using GLP-1 and its analogs for therapeutic treatments of diabetes [for a detailed discussion of GLP-1 physiology, see reviews: 1) Kieffer T J and Habener J F., 1999, *Endocrine reviews*, 20 (6), 876-913; 2) Doyle M E and Egan J M., 2001, *Recent Prog. Horm. Res.*, 56:377-99; 3) Holst J J. 1999, *Trends Endocrinol. Metab.*, 10 (6), 229-235; 4) Perfetti R and Merkel P., 2000., *Eur. J. Endocrinol.*, 143: 717-725; 5) Nauck M A., 1997, *Cur. Opin. Endocrinol. Diabet.*, 4: 291-299; 6) Gutniak M K., 1997, *Intl. Diabet. Monitor.*, 9(2) 1-12; 7) Drucker D J., 2001, *Endocrinol.*, 142 (2) 521-527].

GLP-1 is a 30 aa (amino acid) peptide derived from proglucagon, a 160 aa prohormone. The actions of different prohormone convertases in the pancreas and intestine result in the production of glucagons and other ill-defined peptides, whereas cleavage of proglucagon results in GLP-1 and GLP-2, as well as two other peptides. The amino acid sequence of GLP-1 is 100% homologous in all mammals studied so far, implying a critical physiological role. GLP-1(7-37)OH is C-terminally truncated and amidated to form GLP-1(7-36) $NH_2$. The biological effects and metabolic turnover of the free acid, GLP-1(7-37)OH, and the amide, GLP-1(7-36)$NH_2$, are indistinguishable. By convention, the numbering of the amino acids is based on the processed GLP-1(1-37)OH from the proglucagon peptide. The biologically active GLP-1 is the result of further processing: GLP-1(7-36)$NH_2$. Thus the first amino acid of GLP-1(7-37)OH or GLP-1(7-36)$NH_2$ is His7.

In the gastrointestinal tract, GLP-1 is produced by L-cells of intestinal, colonic and rectal mucosa, in response to stimulation by intraluminal glucose. The plasma half life of active GLP-1 is <5 minutes, and its metabolic clearance rate is around 12-13 minutes (Holst J J., 1994, *Gastroenterology*, 107:1848-1855). The major protease involved in the metabolism of GLP-1 is dipeptidyl peptidase (DPP) IV (CD26) which cleaves the N-terminal His-Ala dipeptide, producing metabolites GLP-1(9-37)OH or GLP-1(9-36)$NH_2$, which are variably described as being inactive, weak agonists or antagonists of the GLP-1 receptor. GLP-1 Receptor (GLP-1 R) is a G protein coupled receptor of 463 aa and is localized in pancreatic beta cells, in the lung, and to a lesser extent in the brain, adipose tissue and kidneys. The stimulation of GLP-1R by GLP-1(7-37)OH or GLP-1(7-36)$NH_2$ results in adenylate cyclase activation, cAMP synthesis, membrane depolarization, rises in intracellular calcium, and increases in glucose-induced insulin secretion (Holz G G et al., 1995, *J. Biol. Chem.*, 270: 17749-57).

GLP-1 is the most potent insulin secretagogue that is secreted from the intestinal mucosa in response to food intake. Fasting levels of immunoreactive GLP-1 in humans are 5-10 pmol/L and rise to 25 pmol/L post-prandially (Perfetti R and Merkel P, 2000 vide supra). The profound incretin effect of GLP-1 is underscored by the fact that GLP-1 R knockout mice are glucose-intolerant (Scrocchi L A et al. 1996, *Nat. Med.* 2: 1254-1258). The incretin response of iv infused GLP-1 is preserved in diabetic subjects, though the incretin response to oral glucose in these patients is compromised. GLP-1 administration by infusion or sc injections not only controlled fasting glucose levels in diabetic patients, but also maintained the glucose threshold for insulin secretion (Gutniak M et al., 1992, *New Engl. J. Med.*, 326: 1316-1322; Nauck M A et al., 1986, Diabetologia, 29: 46-52; Nauck M A et al., 1993, ibid. 36: 741-744). Thus GLP-1 has shown enormous potential as a possible therapeutic agent capable of augmenting insulin secretion in a physiological manner while avoiding hypoglycemia associated with sulfonylurea drugs.

Other important mechanisms of GLP-1 on glucose homeostasis are suppression of glucagon secretion and inhibition of gastric motility (Tolessa T et al., 1998, *J. Clin. Invest.*, 102: 764-774). GLP-1 inhibitory actions on alpha cells of the pancreas lead to decreases in hepatic glucose production via reduction in gluconeogenesis and glycogenolysis (D'Alessio D et al., 1997, *Diabetes*, 46 (Suppl. 1): 29A). This anti-glucagon effect of GLP-1 is preserved in diabetic patients.

The so-called ileal brake effect of GLP-1, wherein gastric motility and gastric secretion are inhibited, is effected via vagal efferent receptors or via direct action on intestinal smooth muscle. Reduction of gastric acid secretion by GLP-1 contributes to a lag phase in nutrient availability, thus obviating the need for a rapid insulin response. In summary, the gastrointestinal effects of GLP-1 contribute significantly to delayed glucose and fatty acid absorption and modulate insulin secretion and glucose homeostasis.

GLP-1 was also shown to induce beta cell specific genes, such as GLUT-1 transporter, insulin receptor (via the interaction of PDX-1 with insulin promoter), and hexokinase-1. Thus GLP-1 has the potential to reverse glucose intolerance normally associated with aging, as demonstrated by rodent experiments (Perfetti R. and Merkel P., 2000, vide supra). In addition, GLP-1 may contribute to beta cell neogenesis and increases in beta cell mass, in addition to the restoration of beta cell function (Wang Y. et al., 1997, *J. Clin. Invest.*, 99:2883-2889; Xu G. et al., 1999, *Diabetes*, 48: 2270-2276).

Central effects of GLP-1 include increases in satiety coupled with a decrease in food intake, effected via the action of hypothalamic GLP-1 R. A 48-hour continuous sc infusion of GLP-1 in type II diabetic subjects decreased hunger and food intake and increased satiety (Toft-Nielsen M B. et al., 1999, *Diabetes Care*, 22: 1137-1143). These anorectic effects were absent in GLP-1R knock out mice (Scrocchi L A. et al., 1996 vide supra).

The pharmacokinetics and pharmacodynamics of GLP-1 (the half life of iv injected peptide in serum is about 2-3 minutes [Vilsboll T. et al., 2003, *J. Clin. Endocrinol. Med.*, 88:220]), as well as the duration of hypoglycemic action (2-3 hours [Nauck M A. et al., 1996, *Diabetologia*, 39:1546; Todd J F. et al., 1998, *Clin. Sci.* 95:325]) are clearly insufficient for qd or bid administration to advanced diabetic patients desirous of glycemic control throughout the day.

International application WO 99/43706 discloses GLP-1 analogs having a lipophilic substituent on at least one lysine residue, allowing the peptides to bind to albumin providing for protracted in vivo action. Analogs of GLP-1 not modified at a lysine residue, were not described as possessing extended duration of action.

International application WO 01/98331 discloses GLP-1 analogs having modifications at one or more of the following positions: 11, 12, 16, 22, 23, 24, 25, 27, 30, 33, 34, 35, 36, and 37. These analogs have been described as having a markedly decreased propensity to aggregate as compared to GLP-1(7-37)OH.

International application WO 03/18516 discloses GLP-1 analogs having modifications at one or more of the following positions: 7, 8, 12, 16, 18, 19, 20, 22, 25, 27, 30, 33, and 37. These analogs have been described as having increased potency, facilitating the use of a delivery technology associated with limited bio-availability.

There thus remains a need to develop potent GLP-1 analogs displaying not only DPPIV resistance but also possessing extended pharmacological duration of action.

The present invention seeks to meet these and other needs.

The present invention refers to a number of documents, the contents of which is herein incorporated by reference in their entirety.

SUMMARY OF THE INVENTION

The present invention relates to novel GLP-1 analogs having improved biological potency as well as extended pharmacological activity. In an embodiment, the present invention relates to GLP-1 analogs (28 or 29 aa long) comprising amino acid substitutions at one or more of the following positions: 8, 20, 27, 30 and 33.

In an embodiment, the present invention relates to GLP-1 analogs comprising the following sequence:

R1-His-X8-Glu-Gly-Thr-Phe-Thr-Ser-Asp-Val-Ser-Ser-Tyr-X20-Glu-Gly-Gln-Ala-Ala-Lys-X27-Phe-Ile-X30-Trp-Leu-X33 (SEQ ID NOs: 1 to 11, depending on the nature of X33).

wherein:

R1 is selected from the group consisting of hydrogen, a linear or branched unsaturated $C_1$-$C_6$ acyl group, an optionally substituted arylcarbonyl, an optionally substituted cycloalkylcarbonyl, and an optionally substituted arylalkylcarbonyl; in an embodiment of the present invention R1 is hydrogen, 2-hydroxybenzoyl or trans-3-hexenoyl;

X8 is selected from the group consisting of Ala, Aib, Val and Gly;

X20 is selected from the group consisting of Leu and Gly, Gly having a $C_6$-$C_{20}$ alkyl side chain; in an embodiment of the present invention X20 is S-octylglycine;

X27 is selected from the group consisting of Ala, Leu, Val, Ile, and Glu;

X30 is selected from the group consisting of Glu, Asp, Asn, Gln, and Ala; and

X33 is selected from the group consisting of Lys-Asn-Aib-OH, Lys-Asn-Aib-$NH_2$, Val-Lys-Asn-OH, Val-Lys-Asn-$NH_2$, Lys-Asn-OH, Lys-Asn-$NH_2$, Val-Lys-Gly-Arg-$NH_2$ (SEQ ID NO: 12), Val-Lys-Aib-Arg-OH (SEQ ID NO: 13), Val-Lys-Aib-Arg-$NH_2$ (SEQ ID NO: 14), Lys-Asn-Gly-OH and Lys-Asn-Gly-$NH_2$, with the proviso that the sequence is not His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-$NH_2$ (SEQ ID NO: 15).

In an embodiment the present invention relates to GLP-1 analogs comprising an amino acid at position 27 selected from the group consisting of alanine (Ala), leucine (Leu), valine (Val), isoleucine (Ile) and glutamic acid (Glu); an amino acid at position 8 selected from the group consisting of alanine (Ala), aminoisobutyric acid (Aib), valine (Val) and glycine (Gly); an amino acid at position 30 selected from the group consisting of glutamic acid (Glu), glutamine (Gln), asparagine (Asn), aspartic acid (Asp), and alanine (Ala); and a C-terminus amino acid sequence of Valine33-Lysine34-Asparagine35-$NH_2$.

In a further embodiment the present invention relates to GLP-1 analogs comprising an R1 selected from hydrogen and 2-hydroxybenzoyl; an amino acid at position 27 selected from the group consisting of alanine (Ala), leucine (Leu), valine (Val), isoleucine (Ile) and glutamic acid (Glu); an amino acid at position 8 selected from the group consisting of alanine (Ala), aminoisobutyric acid (Aib), valine (Val) and glycine (Gly); an amino acid at position 30 selected from the group consisting of glutamic acid (Glu), glutamine (Gln), alanine (Ala), asparagine (Asn) and aspartic acid (Asp); and a C-terminus amino acid sequence of Valine33-Lysine34-Asparagine35-$NH_2$.

In a further embodiment the present invention relates to GLP-1 analogs comprising an R1 selected from 2-hydroxybenzoyl and trans-3-hexenoyl; an amino acid at position 27 selected from the group consisting of alanine (Ala), leucine (Leu), valine (Val), isoleucine (Ile) and glutamic acid (Glu); an amino acid at position 30 selected from the group consisting of glutamic acid (Glu), aspartic acid (Asp), alanine (Ala), glutamine (Gln) and asparagine (Asn); and a C-terminus amino acid sequence of Lysine33-Asparagine34-$NH_2$.

In a further embodiment the present invention relates to GLP-1 analogs comprising an R1 selected from 2-hydroxybenzoyl and trans-3-hexenoyl; an amino acid at position 27 selected from the group consisting of alanine (Ala), leucine (Leu); valine (Val), glutamic acid (Glu), and isoleucine (Ile); an amino acid at position 30 selected from the group consisting of glutamic acid (Glu), glutamine (Gln), aspartic acid (Asp), asparagine (Asn), and alanine (Ala); and a C-terminus amino acid sequence of Lysine33-Asparagine34-Aminoisobutyric acid35-$NH_2$.

In a further embodiment the present invention relates to GLP-1 analogs comprising an R1 selected from hydrogen, 2-hydroxybenzoyl, and trans-3-hexenoyl; an amino acid at position 8 selected from the group consisting of aminoisobutyric acid (Aib), alanine (Ala), valine (Val) and glycine (Gly); an amino acid at position 27 selected from the group consisting of alanine (Ala), leucine (Leu), valine (Val), glutamic acid (Glu) and isoleucine (Ile); an amino acid at position 30 selected from the group consisting of glutamic acid (Glu), aspartic acid (Asp), asparagine (Asn), glutamine (Gln) and alanine (Ala); and a C-terminus amino acid sequence of Lysine33-Asparagine34-Aminoisobutyric acid35-$NH_2$.

In a further embodiment the present invention relates to GLP-1 analogs comprising an R1 selected from hydrogen and trans-3-hexenoyl; an amino acid at position 27 selected from the group consisting of alanine (Ala), leucine (Leu), valine (Val), isoleucine (Ile), and glutamic acid (Glu); an amino acid at position 8 selected from the group consisting of aminoisobutyric acid (Aib), valine (Val), alanine (Ala), and glycine (Gly); an amino acid at position 30 selected from the group consisting of glutamic acid (Glu), glutamine (Gln), aspartic acid (Asp), asparagine (Asn) and alanine (Ala); and a C-terminus amino acid sequence of Lysine33-Asparagine34-NH$_2$.

In a further embodiment the present invention relates to GLP-1 analogs comprising an amino acid at position 20 selected from the group consisting of leucine (Leu) and glycine (Gly) comprising a C$_6$-C$_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); and a C-terminus amino acid sequence of Valine33-Lysine34-Asparagine35-NH$_2$.

In yet a further embodiment the present invention relates to GLP-1 analogs comprising an amino acid at position 20 selected from the group consisting of leucine (Leu) and glycine (Gly) comprising a C$_6$-C$_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); and a C-terminus amino acid sequence of Lysine33-Asparagine34-NH$_2$.

In yet a further embodiment the present invention relates to GLP-1 analogs comprising an amino acid at position 20 selected from the group consisting of leucine (Leu) and glycine (Gly) comprising a C$_6$-C$_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile) and glutamic acid (Glu); and a C-terminus amino acid sequence of Valine33-Lysine34-Asparagine35-NH$_2$.

In yet a further embodiment the present invention relates to GLP-1 analogs comprising an amino acid at position 20 selected from the group consisting of leucine (Leu) and a glycine (Gly) comprising a C$_6$-C$_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile), and glutamic acid (Glu); and a C-terminus amino acid sequence of Lysine33-Asparagine34-NH$_2$.

In yet a further embodiment the present invention relates to GLP-1 analogs comprising an amino acid at position 20 selected from the group consisting of leucine (Leu) and a glycine (Gly) comprising a C$_6$-C$_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile), and glutamic acid (Glu); an amino acid at position 30 selected from the group consisting of glutamic acid (Glu), asparagine (Asn), aspartic acid (Asp), glutamine (Gln) and alanine (Ala); and a C-terminus amino acid sequence of Valine33-Lysine34-Asparagine35-NH$_2$.

In yet a further embodiment the present invention relates to GLP-1 analogs comprising an amino acid at position 20 selected from the group consisting of leucine (Leu) and a glycine (Gly) comprising a C$_6$-C$_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile) and glutamic acid (Glu); an amino acid at position 30 selected from the group consisting of glutamic acid (Glu), aspartic acid (Asp), asparagine (Asn), alanine (Ala) and glutamine (Gln); and a C-terminus amino acid sequence of Lysine33-Asparagine34-NH$_2$.

In yet a further embodiment the present invention relates to GLP-1 analogs comprising an amino acid at position 20 selected from the group consisting of leucine (Leu) and a glycine (Gly) comprising a C$_6$-C$_{20}$ alkyl side chain, which, in an embodiment of the present invention is an octyl chain; an amino acid at position 27 selected from the group consisting of alanine (Ala), leucine (Leu), valine (Val), isoleucine (Ile), and glutamic acid (Glu); an amino acid at position 30 selected from the group consisting of glutamic acid (Glu), aspartic acid (Asp), asparagine (Asn), alanine (Ala) and glutamine (Gln); wherein R1 is trans-3-hexenoyl; and having a C-terminus amino acid sequence of Lysine33-Asparagine34-NH$_2$.

In yet a further embodiment the present invention relates to GLP-1 analogs comprising an R1 selected from hydrogen, 2-hydroxybenzoyl and trans-3-hexenoyl; an amino acid at position 27 selected from the group consisting of alanine (Ala), leucine (Leu), valine (Val), isoleucine (Ile), and glutamic acid (Glu); an amino acid at position 8 selected from the group consisting of aminoisobutyric acid (Aib), valine (Val), alanine (Ala), and glycine (Gly); an amino acid at position 30 selected from the group consisting of glutamic acid (Glu), glutamine (Gln), aspartic acid (Asp), asparagine (Asn) and alanine (Ala); and a C-terminus amino acid sequence of Lysine33-Asparagine34-Glycine35-NH$_2$.

In yet a further embodiment the present invention relates to GLP-1 analogs comprising an R1 selected from 2-hydroxybenzoyl and trans-3-hexenoyl; an amino acid at position 20 selected from the group consisting of leucine (Leu) and glycine (Gly) comprising a C$_6$-C$_{20}$ alkyl side chain, which, in an embodiment of the present invention is an octyl chain; and a C-terminus amino acid sequence of Valine33-Lysine34-Aminoisobutyric acid35-Arginine36-NH$_2$.

In yet a further embodiment the present invention relates to GLP-1 analogs comprising an amino acid at position 20 selected from the group consisting of leucine (Leu) and a glycine (Gly) comprising a C$_6$-C$_{20}$ alkyl side chain, which, in an embodiment of the present invention is an octyl chain; an amino acid at position 27 selected from the group consisting of alanine (Ala), leucine (Leu), valine (Val), isoleucine (Ile), and glutamic acid (Glu); an amino acid at position 30 selected from the group consisting of glutamic acid (Glu), aspartic acid (Asp), asparagine (Asn), alanine (Ala) and glutamine (Gln); wherein R1 is trans-3-hexenoyl; and having a C-terminus amino acid sequence of Lysine33-Asparagine34-NH$_2$.

In an embodiment, the present invention relates to a GLP-1 analog comprising the following sequence:

His-Gly-Glu-Gly-Thr-Phe-Thr-Ser- (SEQ ID NO: 16)

Asp-Val-Ser-Ser-Tyr-Leu-Glu-Gly-

Gln-Ala-Ala-Lys-Ala-Phe-Ile-Glu-

Trp-Leu-Val-Lys-Asn-NH$_2$.

In an embodiment, the present invention relates to a GLP-1 analog comprising the following sequence:

2-Hydroxybenzoyl-NH-His-Ala-Glu- (SEQ ID NO: 17)

Gly-Thr-Phe-Thr-Ser-Asp-Val-Ser-

Ser-Tyr-Leu-Glu-Gly-Gln-Ala-Ala-

Lys-Leu-Phe-Ile-Glu-Trp-Leu-Lys-

Asn-NH$_2$.

In an embodiment, the present invention relates to a GLP-1 analog comprising the following sequence:

```
2-Hydroxybenzoyl-NH-His-Ala-Glu-    (SEQ ID NO: 18)
Gly-Thr-Phe-Thr-Ser-Asp-Val-Ser-
Ser-Tyr-Leu-Glu-Gly-Gln-Ala-Ala-
Lys-Ala-Phe-Ile-Glu-Trp-Leu-Lys-
Asn-Aib-NH₂.
```

In an embodiment, the present invention relates to a GLP-1 analog comprising the following sequence:

```
His-Gly-Glu-Gly-Thr-Phe-Thr-Ser-    (SEQ ID NO: 19)
Asp-Val-Ser-Ser-Tyr-Leu-Glu-Gly-
Gln-Ala-Ala-Lys-Ala-Phe-Ile-Glu-
Trp-Leu-Lys-Asn-NH₂.
```

In an embodiment, the present invention relates to a GLP-1 analog comprising the following sequence:

```
His-Gly-Glu-Gly-Thr-Phe-Thr-Ser-    (SEQ ID NO: 20)
Asp-Val-Ser-Ser-Tyr-[(S)-
Octylglycine]-Glu-Gly-Gln-Ala-Ala-
Lys-Ala-Phe-Ile-Glu-Trp-Leu-Lys-
Asn-NH₂.
```

In an embodiment, the present invention relates to a GLP-1 analog comprising the following sequence:

```
trans-3-hexenoyl-NH-His-Ala-Glu-    (SEQ ID NO: 21)
Gly-Thr-Phe-Thr-Ser-Asp-Val-Ser-
Ser-Tyr-Leu-Glu-Gly-Gln-Ala-Ala-
Lys-Leu-Phe-Ile-Glu-Trp-Leu-Lys-
Asn-NH₂.
```

In an embodiment, the present invention relates to a GLP-1 analog comprising the following sequence:

```
trans-3-hexenoyl-NH-His-Ala-Glu-    (SEQ ID NO: 22)
Gly-Thr-Phe-Thr-Ser-Asp-Val-Ser-
Ser-Tyr-[(S)-Octylglycine]-Glu-
Gly-Gln-Ala-Ala-Lys-Ala-Phe-Ile-
Glu-Trp-Leu-Lys-Asn-NH₂.
```

In an embodiment, the present invention relates to a GLP-1 analog comprising the following sequence:

```
trans-3-hexenoyl-NH-His-Ala-Glu-    (SEQ ID NO: 23)
Gly-Thr-Phe-Thr-Ser-Asp-Val-Ser-
Ser-Tyr-Leu-Glu-Gly-Gln-Ala-Ala-
Lys-Leu-Phe-Ile-Glu-Trp-Leu-Val-
Lys-Asn-NH₂.
```

In an embodiment, the present invention relates to a GLP-1 analog comprising the following sequence:

```
trans-3-hexenoyl-NH-His-Ala-Glu-    (SEQ ID NO: 24)
Gly-Thr-Phe-Thr-Ser-Asp-Val-Ser-
Ser-Tyr-Leu-Glu-Gly-Gln-Ala-Ala-
Lys-Ala-Phe-Ile-Glu-Trp-Leu-Lys-
Asn-NH₂.
```

In an embodiment, the present invention relates to a GLP-1 analog comprising the following sequence:

```
trans-3-hexenoyl-NH-His-Ala-Glu-    (SEQ ID NO: 25)
Gly-Thr-Phe-Thr-Ser-Asp-Val-Ser-
Ser-Tyr-Leu-Glu-Gly-Gln-Ala-Ala-
Lys-Ala-Phe-Ile-Glu-Trp-Leu-Val-
Lys-Asn-NH₂.
```

In an embodiment, the present invention relates to a GLP-1 analog comprising the following sequence:

```
trans-3-hexenoyl-NH-His-Ala-Glu-    (SEQ ID NO: 26)
Gly-Thr-Phe-Thr-Ser-Asp-Val-Ser-
Ser-Tyr-[(S)-Octylglycine]-Glu-
Gly-Gln-Ala-Ala-Lys-Ala-Phe-Ile-
Glu-Trp-Leu-Val-Lys-Asn-NH₂.
```

In an embodiment, the present invention relates to a GLP-1 analog comprising the following sequence:

```
His-Ala-Glu-Gly-Thr-Phe-Thr-Ser-    (SEQ ID NO: 27)
Asp-Val-Ser-Ser-Tyr-[(S)-
Octylglycine]-Glu-Gly-Gln-Ala-Ala-
Lys-Glu-Phe-Ile-Ala-Trp-Leu-Val-
Lys-Gly-Arg-NH₂.
```

In an embodiment, the present invention relates to a GLP-1 analog comprising the following sequence:

```
His-Gly-Glu-Gly-Thr-Phe-Thr-Ser-    (SEQ ID NO: 28)
Asp-Val-Ser-Ser-Tyr-[(S)-
Octylglycine]-Glu-Gly-Gln-Ala-Ala-
Lys-Glu-Phe-Ile-Ala-Trp-Leu-Val-
Lys-Gly-Arg-NH₂.
```

In an embodiment, the present invention relates to a GLP-1 analog comprising the following sequence:

trans-3-hexenoyl-NH-His-Ala-Glu- (SEQ ID No: 29)
Gly-Thr-Phe-Thr-Ser-Asp-Val-Ser-
Ser-Tyr-[(S)-Octylglycine]-Glu-
Gly-Gln-Ala-Ala-Lys-Glu-Phe-Ile-
Ala-Trp-Leu-Val-Lys-Gly-Arg-NH$_2$.

In an embodiment, the present invention relates to a GLP-1 analog comprising the following sequence:

trans-3-hexenoyl-NH-His-Ala-Glu- (SEQ ID No: 30)
Gly-Thr-Phe-Thr-Ser-Asp-Val-Ser-
Ser-Tyr-[(S)-Octylglycine]-Glu-
Gly-Gln-Ala-Ala-Lys-Glu-Phe-Ile-
Ala-Trp-Leu-Val-Lys-Aib-Arg-NH$_2$.

In an embodiment, the present invention relates to a GLP-1 analog comprising the following sequence:

2-Hydroxybenzoyl-NH-His-Ala-Glu- (SEQ ID NO: 31)
Gly-Thr-Phe-Thr-Ser-Asp-Val-
Ser-Ser-Tyr-Leu-Glu-Gly-Gln-Ala-
Ala-Lys-Leu-Phe-Ile-Glu-Trp-Leu-
Lys-Asn-Gly-NH$_2$.

In an embodiment, the present invention relates to a GLP-1 analog comprising the following sequence:

His-Gly-Glu-Gly-Thr-Phe-Thr-Ser- (SEQ ID NO: 32)
Asp-Val-Ser-Ser-Tyr-Leu-Glu-Gly-
Gln-Ala-Ala-Lys-Leu-Phe-Ile-Glu-
Trp-Leu-Lys-Asn-NH$_2$.

In an embodiment, the present invention relates to a GLP-1 analog comprising the following sequence:

His-Gly-Glu-Gly-Thr-Phe-Thr-Ser- (SEQ ID NO: 33)
Asp-Val-Ser-Ser-Tyr-Leu-Glu-Gly-
Gln-Ala-Ala-Lys-Leu-Phe-Ile-Glu-
Trp-Leu-Val-Lys-Asn-NH$_2$.

In an embodiment, the present invention relates to a GLP-1 analog comprising the following sequence:

trans-3-hexenoyl-NH-His-Ala-Glu- (SEQ ID NO: 34)
Gly-Thr-Phe-Thr-Ser-Asp-Val-Ser-
Ser-Tyr-[(S)-Octylglycine]-Glu-
Gly-Gln-Ala-Ala-Lys-Leu-Phe-Ile-
Glu-Trp-Leu-Lys-Asn-NH$_2$.

In an embodiment, the present invention relates to a GLP-1 analog comprising the following sequence:

trans-3-hexenoyl-NH-His-Ala-Glu- (SEQ ID NO: 35)
Gly-Thr-Phe-Thr-Ser-Asp-Val-Ser-
Ser-Tyr-[(S)-Octylglycine]-Glu-
Gly-Gln-Ala-Ala-Lys-Leu-Phe-Ile-
Glu-Trp-Leu-Val-Lys-Asn-NH$_2$.

In an embodiment, the present invention relates to a GLP-1 analog comprising the following sequence:

His-Gly-Glu-Gly-Thr-Phe-Thr-Ser- (SEQ ID NO: 36)
Asp-Val-Ser-Ser-Tyr-[(S)-
Octylglycine]-Glu-Gly-Gln-Ala-Ala-
Lys-Leu-Phe-Ile-Glu-Trp-Leu-Lys-
Asn-NH$_2$.

In an embodiment, the present invention relates to a GLP-1 analog comprising the following sequence:

His-Gly-Glu-Gly-Thr-Phe-Thr-Ser- (SEQ ID NO: 37)
Asp-Val-Ser-Ser-[(S)-
Octylglycine]-Leu-Glu-Gly-Gln-Ala-
Ala-Lys-Ala-Phe-Ile-Glu-Trp-Leu-
Lys-Asn-NH$_2$.

In an embodiment, the present invention relates to a GLP-1 analog comprising the following sequence:

His-Ala-Glu-Gly-Thr-Phe-Thr- (SEQ ID NO: 38)
Ser-Asp-Val-Ser-Ser-Tyr-[(R)-
Octadecylglycine]-Glu-Gly-Gln-
Ala-Ala-Lys-Glu-Phe-Ile-Ala-Trp-
Leu-Val-Lys-Gly-Arg-NH$_2$.

The present invention also relates to a composition comprising a therapeutically effective amount of a peptide as described herein, or a pharmaceutically acceptable salt thereof, in association with at least one constituent selected from the group consisting of pharmaceutically acceptable carriers, diluents and excipients. In an embodiment, the present invention relates to a composition comprising a therapeutically effective amount of a peptide as described herein, or a pharmaceutically acceptable salt thereof, wherein the therapeutically effective amount is ranging from about 1 mcg to about 10 mg, or any range derivable therein.

The present invention also relates to a composition comprising a prophylactically effective amount of a peptide as described herein, or a pharmaceutically acceptable salt thereof, in association with at least one constituent selected from the group consisting of pharmaceutically acceptable carriers, diluents and excipients.

The present invention further relates to a method of treating a disease or condition associated with a disorder of glucose metabolism. Moreover, the present invention relates to a method of preventing (e.g. prophylaxis) a disease or condition associated with a disorder of glucose metabolism. Non-limiting examples of glucose disorders include: diabetes mellitus of Type I or Type II, insulin resistance, as well as weight disorders and diseases or conditions associated therewith. Non-limiting examples of weight disorders or associated conditions include obesity, overweight-associated conditions, satiety deregulation, reduced plasma insulin levels, increased blood glucose levels, and reduced pancreatic beta cell mass.

In an embodiment, the present invention relates to a method for treating diabetes mellitus of Type I or Type II, comprising administering to a subject in need of such treatment a therapeutically effective amount of a peptide as described herein, or a pharmaceutically acceptable salt thereof.

In an embodiment, the present invention relates to a method for treating insulin resistance, comprising administering to a subject in need of such treatment a therapeutically effective amount of a peptide as described herein, or a pharmaceutically acceptable salt thereof.

In an embodiment, the present invention relates to a method for weight lowering of a subject, comprising administering to a subject in need of weight lowering an effective amount of a peptide as described herein, or a pharmaceutically acceptable salt thereof.

In an embodiment, the present invention relates to a method for reducing satiety of a subject, comprising administering a therapeutically effective amount of a peptide as described herein, or a pharmaceutically acceptable salt thereof, to a subject in need thereof.

In an embodiment, the present invention relates to a method for post-prandially increasing plasma insulin levels in a subject, comprising administering a therapeutically effective amount of a peptide as described herein, or a pharmaceutically acceptable salt thereof, to a subject in need thereof.

In an embodiment, the present invention relates to a method for reducing fasting blood glucose levels in a subject, comprising administering a therapeutically effective amount of a peptide as described herein, or a pharmaceutically acceptable salt thereof, to a subject in need thereof.

In an embodiment, the present invention relates to a method for increasing pancreatic beta cell mass in a subject, comprising administering a therapeutically effective amount of a peptide as described herein, or a pharmaceutically acceptable salt thereof, to a subject in need thereof.

In yet another embodiment, the present invention relates to methods for administering the peptides, or pharmaceutically acceptable salts thereof, as described herein. Non-limiting examples of methods for administering the peptides, or pharmaceutically acceptable salts thereof, include subcutaneous, intravenous, transdermal, oral, bucal, and intranasal.

The present invention further relates to a use of a GLP-1 analog, or a pharmaceutically acceptable salt thereof, for treating or preventing a disorder or condition associated with glucose metabolism.

In a further embodiment, the present invention relates to a use of the peptides as described herein, or pharmaceutically acceptable salts thereof, for treating diabetes mellitus of Type I or Type II in a subject.

In a further embodiment, the present invention relates to a use of the peptides as described herein, or pharmaceutically acceptable salts thereof, for treating insulin resistance in a subject.

In a further embodiment, the present invention relates to a use of the peptides as described herein, or pharmaceutically acceptable salts thereof, for lowering weight of a subject.

In a further embodiment, the present invention relates to a use of the peptides as described herein, or pharmaceutically acceptable salts thereof, for reducing satiety of a subject.

In a further embodiment, the present invention relates to a use of the peptides as described herein, or pharmaceutically acceptable salts thereof, for post-prandially increasing plasma insulin levels in a subject.

In a further embodiment, the present invention relates to a use of the peptides as described herein, or pharmaceutically acceptable salts thereof, for reducing fasting blood glucose levels in a subject.

In a further embodiment, the present invention relates to a use of the peptides as described herein, or pharmaceutically acceptable salts thereof, for increasing pancreatic beta cell mass in a subject.

In a further embodiment, the present invention relates to a use of the peptides as described herein, or pharmaceutically acceptable salts thereof, for preparing a medicament for treating diabetes mellitus of Type I or Type II in a subject.

In a further embodiment, the present invention relates to a use of the peptides as described herein, or pharmaceutically acceptable salts thereof, for preparing a medicament for treating insulin resistance in a subject.

In a further embodiment, the present invention relates to a use of the peptides as described herein, or pharmaceutically acceptable salts thereof, for preparing a medicament for weight lowering of a subject.

In a further embodiment, the present invention relates to a use of the peptides as described herein, or pharmaceutically acceptable salts thereof, for preparing a medicament for increasing satiety of a subject.

In a further embodiment, the present invention relates to a use of the peptides as described herein, or pharmaceutically acceptable salts thereof, for preparing a medicament for post-prandially increasing plasma insulin levels in a subject.

In a further embodiment, the present invention relates to a use of the peptides as described herein, or pharmaceutically acceptable salts thereof, for preparing a medicament for reducing fasting blood glucose levels in a subject.

In yet a further embodiment, the present invention relates to a use of the peptides as described herein, or pharmaceutically acceptable salts thereof, for preparing a medicament for increasing pancreatic beta cell mass in a subject.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Further scope and applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

Having thus generally described the invention, reference will now be made to the accompanying drawings, showing by way of illustration a preferred embodiment thereof, and in which:

FIG. 12 (2 hours) and FIGS. 13 and 14 (6 hours). CD-1 mice were treated with streptozotocin and 24 hours later (with a glycemia greater then 20 mmol/L) treated with an analogue and allowed to eat ad libidum for the duration of the experiment (2 and 6 hours). At 10:00 am, the animals were injected subcutaneously with vehicle or GLP-1 analogs. Blood glucose levels were measured for 2 and 6 hours post-injection (mean ±SEM; upper panel). The AUC glucose for a 2 or 6 hour period is presented as a bar (mean ±SEM; lower panel; n is the number of animals as presented on top of the lower panel bars);

FIG. 15 (12 hours). In order to assess the duration of the effects of selected analogs, CD-1 mice were treated with streptozotocin and 24 hours later (with a glycemia greater then 20 mmol/L) treated with an analogue and allowed to eat ad libidum for the duration of the experiment (12 hours). At 10:00 am, the animals were injected subcutaneously with vehicle or GLP-1 analogs. Blood glucose levels were measured for 12 hours post-injection (mean ±SEM; upper panel). The AUC glucose for the 12 hour period is presented after subtracting the fed glucose AUC of normal mice (mean ±SEM; lower panel; n is the number of animals as presented on top of the lower panel bars);

Figure 1:
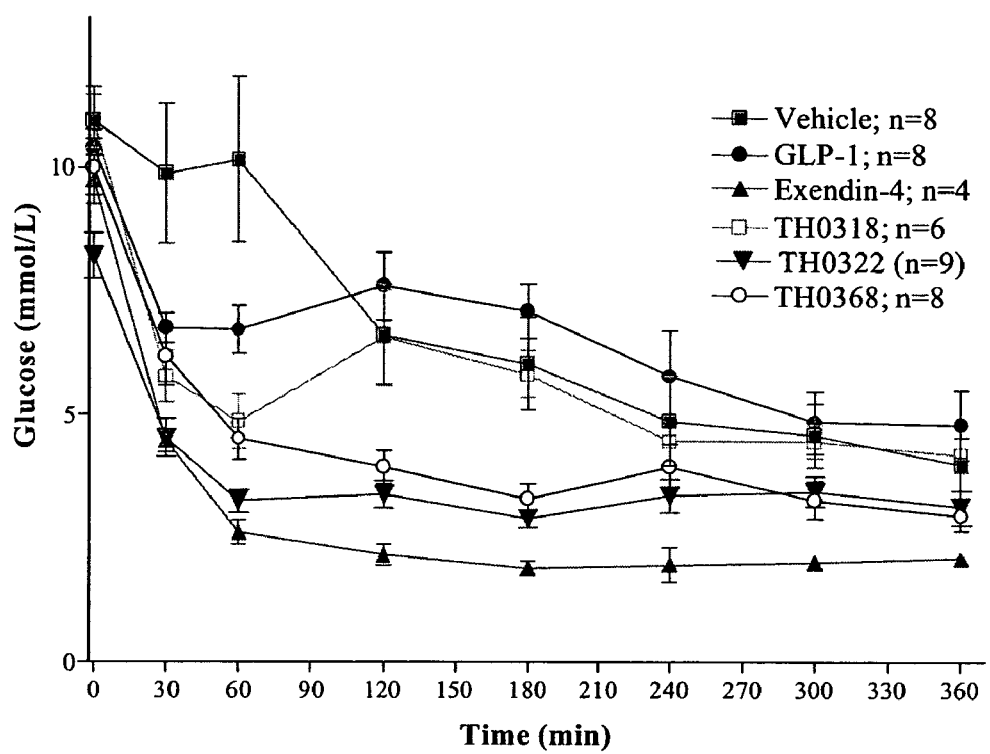
FIG. 1 shows blood glucose levels in CD-1 mice that were fasted overnight and fed for 30 minutes. Various peptides, including peptides of the present invention (400 μg/kg), were administered sc at 30 minutes and the blood glucose levels were determined for the next 6 hours. The data are presented as mean ±SEM values.

Other objects, advantages and features of the present invention will become more apparent upon reading of the following non-restrictive description of preferred embodiments with reference to the accompanying drawing which is exemplary and should not be interpreted as limiting the scope of the present invention.

DETAILED DESCRIPTION OF THE INVENTION

The following abbreviations have been used throughout the present specification:

DMF: N,N-Dimethylformamide; DIEA: Diisopropylethylamine; TFA: Trifluoroacetic acid; BOP: Benzotriazole-1-yl-oxy-tris(dimethylamino) phosphonium hexafluorophosphate; MALDI-TOF: Matrix Assisted Laser Desorption/Ionisation Mass Spectrometry; HPLC: High Performance Liquid Chromatography; BHA: Benzhydrylamine resin; Boc: t-Butoxycarbonyl; Aib: Aminoisobutyric acid; Pbf: 2,2,4,6,7-Pentamethyldihydrobenzofurane-5-sulfonyl; AUC: Area under the Curve; Nle: Norleucine.

"Aryl" as used herein means an aromatic carbocyclic radical or a substituted aromatic carbocyclic radical containing from 6 to 10 carbon atoms. Non limiting examples are phenyl or naphtyl. Non limiting examples of substituents are $C_1$-$C_6$; straight or branched alkyl such as methyl, ethyl, propyl, isopropyl, butyl, isobutyl, sec-butyl, pentyl, hexyl; and alkenyl, hydroxyl, alkoxy, amino, halo.

"Alkyl" as used herein means a straight or branched $C_1$-$C_6$ aliphatic hydrocarbon group. Non limiting examples of substituents are $C_1$-$C_6$; straight or branched alkyl such as methyl, ethyl, propyl, isopropyl, butyl, isobutyl, sec-butyl, pentyl, hexyl; and alkenyl, hydroxyl, alkoxy, amino, halo.

"Unsaturated acyl" as used herein means an alkenyl carbonyl group where alkenyl means an alkyl group containing a carbon-carbon double bond or triple bond and having from 2 to 5 carbon atoms in the linear chain. Non limiting examples include a trans-3-hexenoyl.

"Aralkyl" as used herein means an alkyl radical in which a hydrogen is substituted for an aryl group. Non limiting examples include benzyl and 3-phenylpropyl.

"Cycloalkyl" as used herein means a non-aromatic ring composed from 3 to 10 carbon atoms, non limiting examples of which are cyclopropyl, cyclobutyl, cyclopentyl, cyclohexyl, cycloheptyl, cyclooctyl, cyclononyl and cyclodecyl, and the cyclic alkyl may be partially unsaturated.

As used herein, the term "carriers", "diluents", "excipients" and "pharmaceutically acceptable salt" are to be construed as defined in the reference manual: "Handbook of Pharmaceutical Excipients" third edition, Arthur H. Kibbe, American Pharmaceutical Association, Pharmaceutical Press, 2000.

So far it has not been possible to confer extended pharmacological activity to GLP-1(7-36) without non-covalent or covalent attachment to albumin. It was discovered, as disclosed herein, that shorter GLP-1 analogs (28 or 29 aa long) comprising amino acid substitutions at one or more of positions 8, 20, 27, 30 or 33, and optionally an N-terminal substituent R1, provide GLP-1(7-34) and GLP-1(7-35) derivatives possessing extended pharmacological activity in vivo (6 h). The shorter GLP-1 analogs (28 or 29 aa long) were prepared by making truncations and amino acid substitutions to the native GLP-1(7-36) amide. The GLP-1 analogs, modified at one or more of the positions 8, 20, 27, 30 and 33, are suitable for qd or bid administration to diabetic patients.

The present invention relates to novel GLP-1 analogs comprising amino acid substitutions at one or more positions 8, 20, 27, 30 or 33, and optionally an N-terminal substituent R1.

The present invention relates to novel GLP-1 analogs comprising improved biological potency as well as extended duration of action on blood glucose levels. Furthermore, the present invention relates to novel GLP-1 analogs displaying not only DPPIV resistance but also having prolonged pharmacological action, comparable to Exendin-4™.

The amino acids as described herein, are identified by the conventional three-letter abbreviations as indicated below in Table 1, and which are as generally accepted in the peptide art as recommended by the IUPAC-IUB commission in biochemical nomenclature:

TABLE 1

Amino acid codes

| Name | 3-letter code | 1-letter code |
|---|---|---|
| Alanine | Ala | A |
| Arginine | Arg | R |
| Asparagine | Asn | N |
| Aspartic | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

By convention, the first amino acid of active GLP-1(His) is numbered 7 and so on.

The term "subject" as used herein is understood as including any mammal. In an embodiment of the present invention, the subject is a human.

In an embodiment, the present invention relates to GLP-1 analogs comprising the following sequence:

R1-His-X8-Glu-Gly-Thr-Phe-Thr-Ser-Asp-Val-Ser-Ser-

Tyr-X20-Glu-Gly-Gln-Ala-Ala-Lys-X27-Phe-Ile-X30-

Trp-Leu-X33 wherein:

R1 is selected from the group consisting of hydrogen, a linear or branched unsaturated $C_1$-$C_6$ acyl group, an optionally substituted arylcarbonyl, an optionally substituted cycloalkylcarbonyl, and an optionally substituted arylalkylcarbonyl; in an embodiment of the present invention R1 is hydrogen, 2-hydroxybenzoyl or trans-3-hexenoyl;

X8 is selected from the group consisting of Ala, Aib, Val and Gly;

X20 is selected from the group consisting of Leu and Gly, Gly having a $C_6$-$C_{20}$ alkyl side chain; in an embodiment of the present invention X20 is preferably S-Octylglycine;

X27 is selected from the group consisting of Ala, Leu, Val, Ile and Glu;

X30 is selected from the group consisting of Glu, Asp, Asn, Gln and Ala; and

X33 is selected from the group consisting of Lys-Asn-Aib-OH, Lys-Asn-Aib-NH$_2$, Val-Lys-Asn-OH, Val-Lys-Asn-NH$_2$, Lys-Asn-OH, Lys-Asn-NH$_2$ and Val-Lys-Gly-Arg-NH$_2$, Val-Lys-Aib-Arg-OH, Val-Lys-Aib-Arg-NH$_2$, Lys-Asn-Gly-OH and Lys-Asn-Gly-NH$_2$;

with the proviso that the sequence is not His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg.

In an embodiment, the present invention relates to GLP-1 analogs having an amino acid at position 27 selected from the group consisting of alanine (Ala), leucine (Leu), valine (Val), isoleucine (Ile) and glutamic acid (Glu); an amino acid at position 8 selected from the group consisting of alanine (Ala), aminoisobutyric acid (Aib), valine (Val) and glycine (Gly); an amino acid at position 30 selected from the group consisting of glutamic acid (Glu), glutamine (Gln), asparagine (Asn), aspartic acid (Asp), and alanine (Ala); and a C-terminus amino acid sequence of Valine33-Lysine34-Asparagine35-NH$_2$.

In a further embodiment, the present invention relates to GLP-1 analogs having an R1 selected from hydrogen and 2-hydroxybenzoyl; an amino acid at position 27 selected from the group consisting of alanine (Ala), leucine (Leu), valine (Val), isoleucine (Ile) and glutamic acid (Glu); an amino acid at position 8 selected from the group consisting of alanine (Ala), aminoisobutyric acid (Aib), valine (Val) and glycine (Gly); an amino acid at position 30 selected from the group consisting of glutamic acid (Glu), glutamine (Gln), alanine (Ala), asparagine (Asn) and aspartic acid (Asp); and a C-terminus amino acid sequence of Valine33-Lysine34-Asparagine35-NH$_2$.

In a further embodiment, the present invention relates to GLP-1 analogs having an R1 selected from 2-hydroxybenzoyl and trans-3-hexenoyl; an amino acid at position 27 selected from the group consisting of alanine (Ala), leucine (Leu), valine (Val), isoleucine (Ile) and glutamic acid (Glu); an amino acid at position 30 selected from the group consisting of glutamic acid (Glu), aspartic acid (Asp), alanine (Ala), glutamine (Gln) and asparagine (Asn); and a C-terminus amino acid sequence of Lysine33-Asparagine34-NH$_2$.

In a further embodiment, the present invention relates to GLP-1 analogs having an R1 selected from 2-hydroxybenzoyl and trans-3-hexenoyl; an amino acid at position 27 selected from the group consisting of alanine (Ala), leucine (Leu); valine (Val), glutamic acid (Glu), and isoleucine (Ile); an amino acid at position 30 selected from the group consisting of glutamic acid (Glu), glutamine (Gln), aspartic acid (Asp), asparagine (Asn), and alanine (Ala); and a C-terminus amino acid sequence of Lysine33-Asparagine34-Aminoisobutyric acid35-NH$_2$.

In a further embodiment, the present invention relates to GLP-1 analogs having an R1 selected from hydrogen, 2-hydroxybenzoyl and trans-3-hexenoyl; an amino acid at position 8 selected from the group consisting of aminoisobutyric acid (Aib), alanine (Ala), valine (Val) and glycine (Gly); an amino acid at position 27 selected from the group consisting of alanine (Ala), leucine (Leu), valine (Val), glutamic acid (Glu) and isoleucine (Ile); an amino acid at position 30 selected from the group consisting of glutamic acid (Glu), aspartic acid (Asp), asparagine (Asn), glutamine (Gln) and alanine (Ala); and a C-terminus amino acid sequence of Lysine33-Asparagine34-Aminoisobutyric acid35-NH$_2$.

In a further embodiment, the present invention relates to GLP-1 analogs having an R1 selected from hydrogen and trans-3-hexenoyl; an amino acid at position 27 selected from the group consisting of alanine (Ala), leucine (Leu), valine (Val), isoleucine (Ile), and glutamic acid (Glu); an amino acid at position 8 selected from the group consisting of aminoisobutyric acid (Aib), valine (Val), alanine (Ala), and glycine (Gly); an amino acid at position 30 selected from the group consisting of glutamic acid (Glu), glutamine (Gln), aspartic acid (Asp), asparagine (Asn) and alanine (Ala); and a C-terminus amino acid sequence of Lysine33-Asparagine34-NH$_2$.

In a further embodiment, the present invention relates to GLP-1 analogs having an amino acid at position 20 selected from the group consisting of leucine (Leu) and glycine (Gly) comprising a $C_6$-$C_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); and a C-terminus amino acid sequence of Valine33-Lysine34-Asparagine35-NH$_2$.

In yet a further embodiment, the present invention relates to GLP-1 analogs having an amino acid at position 20 selected from the group consisting of leucine (Leu) and glycine (Gly) comprising a $C_6$-$C_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); and a C-terminus amino acid sequence of Lysine33-Asparagine34-NH$_2$.

In yet a further embodiment, the present invention relates to GLP-1 analogs having an amino acid at position 20 selected from the group consisting of leucine (Leu) and glycine (Gly) comprising a $C_6$-$C_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile) and glutamic acid (Glu); and a C-terminus amino acid sequence of Valine33-Lysine34-Asparagine35-NH$_2$.

In yet a further embodiment, the present invention relates to GLP-1 analogs having an amino acid at position 20 selected from the group consisting of leucine (Leu) and a glycine (Gly) comprising a $C_6$-$C_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile), and glutamic acid (Glu); and a C-terminus amino acid sequence of Lysine33-Asparagine34-NH$_2$.

In yet a further embodiment, the present invention relates to GLP-1 analogs having an amino acid at position 20 selected from the group consisting of leucine (Leu) and a glycine (Gly) comprising a $C_6$-$C_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile), and glutamic acid (Glu); an amino acid at position 30 selected from the group consisting of glutamic acid (Glu), asparagine (Asn), aspartic acid (Asp), glutamine (Gln) and alanine (Ala); and a C-terminus amino acid sequence of Valine33-Lysine34-Asparagine35-NH$_2$.

In yet a further embodiment, the present invention relates to GLP-1 analogs having an amino acid at position 20 selected from the group consisting of leucine (Leu) and a glycine (Gly) comprising a $C_6$-$C_{20}$ alkyl side chain, which, in an embodiment of the present invention is an octyl chain; an amino acid at position 8 selected from the group consisting of alanine (Ala), aminoisobutyric acid (Aib), valine (Val) and glycine (Gly); an amino acid at position 27 selected from the group consisting of alanine (Ala), leucine (Leu), valine (Val), isoleucine (Ile) and glutamic acid (Glu); an amino acid at position 30 selected from the group consisting of glutamic acid (Glu), aspartic acid (Asp), asparagine (Asn), alanine (Ala) and glutamine (Gln); and a C-terminus amino acid sequence of Lysine33-Asparagine34-$NH_2$.

In yet a further embodiment, the present invention relates to GLP-1 analogs having an amino acid at position 20 selected from the group consisting of leucine (Leu) and a glycine (Gly) comprising a $C_6$-$C_{20}$ alkyl side chain, which, in an embodiment of the present invention is an octyl chain; an amino acid at position 27 selected from the group consisting of alanine (Ala), leucine (Leu), valine (Val), isoleucine (Ile), and glutamic acid (Glu); an amino acid at position 30 selected from the group consisting of glutamic acid (Glu), aspartic acid (Asp), asparagine (Asn), alanine (Ala) and glutamine (Gln); wherein R1 is trans-3-hexenoyl; and having a C-terminus amino acid sequence of Lysine33-Asparagine34-$NH_2$.

In yet a further embodiment, the present invention relates to GLP-1 analogs having an R1 selected from hydrogen, 2-hydroxybenzoyl and trans-3-hexenoyl; an amino acid at position 27 selected from the group consisting of alanine (Ala), leucine (Leu), valine (Val), isoleucine (ile), and glutamic acid (Glu); an amino acid at position 8 selected from the group consisting of aminoisobutyric acid (Aib), valine (Val), alanine (Ala), and glycine (Gly); an amino acid at position 30 selected from the group consisting of glutamic acid (Glu), glutamine (Gin), aspartic acid (Asp), asparagine (Asn) and alanine (Ala); and a C-terminus amino acid sequence of Lysine33-Asparagine34-Glycine35-$NH_2$.

In yet a further embodiment, the present invention relates to GLP-1 analogs having an R1 selected from 2-hydroxybenzoyl and trans-3-hexenoyl; an amino acid at position 20 selected from the group consisting of leucine (Leu) and glycine (Gly) comprising a $C_6$-$C_{20}$ alkyl side chain, which, in an embodiment of the present invention is an octyl chain; and a C-terminus amino acid sequence of Valine33-Lysine34-Aminoisobutyric acid35-Arginine36-$NH_2$.

In yet a further embodiment, the present invention relates to GLP-1 analogs having an amino acid at position 20 selected from the group consisting of leucine (Leu) and a glycine (Gly) comprising a $C_6$-$C_{20}$ alkyl side chain, which, in an embodiment of the present invention is an octyl chain; an amino acid at position 27 selected from the group consisting of alanine (Ala), leucine (Leu), valine (Val), isoleucine (Ile), and glutamic acid (Glu); an amino acid at position 30 selected from the group consisting of glutamic acid (Glu), aspartic acid (Asp), asparagine (Asn), alanine (Ala) and glutamine (Gln); wherein R1 is trans-3-hexenoyl; and having a C-terminus amino acid sequence of Lysine33-Asparagine34-$NH_2$.

In an embodiment, the present invention relates to a GLP-1 analog comprising the following sequence:

His-Gly-Glu-Gly-Thr-Phe-Thr-Ser-   (SEQ. ID NO: 1)
Asp-Val-Ser-Ser-Tyr-Leu-Glu-Gly-
Gln-Ala-Ala-Lys-Ala-Phe-Ile-Glu-
Trp-Leu-Val-Lys-Asn-NH₂.

In an embodiment, the present invention relates to a GLP-1 analog comprising the following sequence:

2-Hydroxybenzoyl-NH-His-Ala-Glu-   (SEQ. ID NO: 2)
Gly-Thr-Phe-Thr-Ser-Asp-Val-
Ser-Ser-Tyr-Leu-Glu-Gly-Gln-Ala-
Ala-Lys-Leu-Phe-Ile-Glu-Trp-Leu-
Lys-Asn-NH₂.

In an embodiment, the present invention relates to a GLP-1 analog comprising the following sequence:

2-Hydroxybenzoyl-NH-His-Ala-Glu-   (SEQ. ID NO: 3)
Gly-Thr-Phe-Thr-Ser-Asp-Val-Ser-
Ser-Tyr-Leu-Glu-Gly-Gln-Ala-Ala-
Lys-Ala-Phe-Ile-Glu-Trp-Leu-Lys-
Asn-Aib-NH₂.

In an embodiment, the present invention relates to a GLP-1 analog comprising the following sequence:

His-Gly-Glu-Gly-Thr-Phe-Thr-Ser-   (SEQ. ID NO: 4)
Asp-Val-Ser-Ser-Tyr-Leu-Glu-Gly-
Gln-Ala-Ala-Lys-Ala-Phe-Ile-Glu-
Trp-Leu-Lys-Asn-NH₂.

In an embodiment, the present invention relates to a GLP-1 analog comprising the following sequence:

His-Gly-Glu-Gly-Thr-Phe-Thr-Ser-   (SEQ. ID NO: 5)
Asp-Val-Ser-Ser-Tyr-[(S)-
Octylglycine]-Glu-Gly-Gln-Ala-Ala-
Lys-Ala-Phe-Ile-Glu-Trp-Leu-Lys-
Asn-NH₂.

In an embodiment, the present invention relates to a GLP-1 analog comprising the following sequence:

trans-3-N H-hexenoyl-His-Ala-Glu-  (SEQ. ID NO: 6)
Gly-Thr-Phe-Thr-Ser-Asp-Val-Ser-
Ser-Tyr-Leu-Glu-Gly-Gln-Ala-Ala-
Lys-Leu-Phe-Ile-Glu-Trp-Leu-Lys-
Asn-NH₂.

In an embodiment, the present invention relates to a GLP-1 analog comprising the following sequence:

trans-3-hexenoyl-NH-His-Ala-Glu-   (SEQ. ID NO: 7)
Gly-Thr-Phe-Thr-Ser-Asp-Val-Ser-
Ser-Tyr-[(S)-Octylglycine]-Glu-
Gly-Gln-Ala-Ala-Lys-Ala-Phe-Ile-
Glu-Trp-Leu-Lys-Asn-NH₂.

In an embodiment, the present invention relates to a GLP-1 analog comprising the following sequence:

trans-3-hexenoyl-NH-His-Ala-Glu- (SEQ. ID NO: 8)
Gly-Thr-Phe-Thr-Ser-Asp-Val-Ser-
Ser-Tyr-Leu-Glu-Gly-Gln-Ala-Ala-
Lys-Leu-Phe-Ile-Glu-Trp-Leu-Val-
Lys-Asn-NH$_2$.

In an embodiment, the present invention relates to a GLP-1 analog comprising the following sequence:

trans-3-hexenoyl-NH-His-Ala-Glu- (SEQ. ID NO: 9)
Gly-Thr-Phe-Thr-Ser-Asp-Val-Ser-
Ser-Tyr-Leu-Glu-Gly-Gln-Ala-Ala-
Lys-Ala-Phe-Ile-Glu-Trp-Leu-Lys-
Asn-NH$_2$.

In an embodiment, the present invention relates to a GLP-1 analog comprising the following sequence:

trans-3-hexenoyl-NH-His-Ala-Glu- (SEQ. ID NO: 10)
Gly-Thr-Phe-Thr-Ser-Asp-Val-Ser-
Ser-Tyr-Leu-Glu-Gly-Gln-Ala-Ala-
Lys-Ala-Phe-Ile-Glu-Trp-Leu-Val-
Lys-Asn-NH$_2$.

In an embodiment, the present invention relates to a GLP-1 analog comprising the following sequence:

trans-3-hexenoyl-NH-His-Ala-Glu- (SEQ. ID NO: 11)
Gly-Thr-Phe-Thr-Ser-Asp-Val-Ser-
Ser-Tyr-[(S)-Octylglycine]-Glu-
Gly-Gln-Ala-Ala-Lys-Ala-Phe-Ile-
Glu-Trp-Leu-Val-Lys-Asn-NH$_2$.

In an embodiment, the present invention relates to a GLP-1 analog comprising the following sequence:

His-Ala-Glu-Gly-Thr-Phe-Thr-Ser- (SEQ. ID NO: 12)
Asp-Val-Ser-Ser-Tyr-[(S)-
Octylglycine]-Glu-Gly-Gln-Ala-Ala-
Lys-Glu-Phe-Ile-Ala-Trp-Leu-Val-
Lys-Gly-Arg-NH$_2$.

In an embodiment, the present invention relates to a GLP-1 analog comprising the following sequence:

His-Gly-Glu-Gly-Thr-Phe-Thr-Ser- (SEQ. ID NO: 13)
Asp-Val-Ser-Ser-Tyr-[(S)-
octylglycine]-Glu-Gly-Gln-Ala-Ala-
Lys-Glu-Phe-Ile-Ala-Trp-Leu-Val-
Lys-Gly-Arg-NH$_2$.

In an embodiment, the present invention relates to a GLP-1 analog comprising the following sequence:

trans-3-hexenoyl-NH-His-Ala-Glu- (SEQ. ID No: 14)
Gly-Thr-Phe-Thr-Ser-Asp-Val-Ser-
Ser-Tyr-[(S)-Octylglycine]-Glu-
Gly-Gln-Ala-Ala-Lys-Glu-Phe-Ile-
Ala-Trp-Leu-Val-Lys-Gly-Arg-NH$_2$.

In an embodiment, the present invention relates to a GLP-1 analog comprising the following sequence:

trans-3-hexenoyl-NH-His-Ala-Glu- (SEQ. ID No: 15)
Gly-Thr-Phe-Thr-Ser-Asp-Val-Ser-
Ser-Tyr-[(S)-Octylglycine]-Glu-
Gly-Gln-Ala-Ala-Lys-Glu-Phe-Ile-
Ala-Trp-Leu-Val-Lys-Aib-Arg-NH$_2$.

In an embodiment, the present invention relates to a GLP-1 analog comprising the following sequence:

2-Hydroxybenzoyl-NH-His-Ala-Glu- (SEQ. ID NO: 16)
Gly-Thr-Phe-Thr-Ser-Asp-Val-Ser-
Ser-Tyr-Leu-Glu-Gly-Gln-Ala-Ala-
Lys-Leu-Phe-Ile-Glu-Trp-Leu-Lys-
Asn-Gly-NH$_2$.

In an embodiment, the present invention relates to a GLP-1 analog comprising the following sequence:

His-Gly-Glu-Gly-Thr-Phe-Thr-Ser- (SEQ. ID NO: 17)
Asp-Val-Ser-Ser-Tyr-Leu-Glu-Gly-
Gln-Ala-Ala-Lys-Leu-Phe-Ile-Glu-
Trp-Leu-Lys-Asn-NH$_2$.

In an embodiment, the present invention relates to a GLP-1 analog comprising the following sequence:

His-Gly-Glu-Gly-Thr-Phe-Thr-Ser- (SEQ. ID NO: 18)
Asp-Val-Ser-Ser-Tyr-Leu-Glu-Gly-
Gln-Ala-Ala-Lys-Leu-Phe-Ile-Glu-
Trp-Leu-Val-Lys-Asn-NH$_2$.

In an embodiment, the present invention relates to a GLP-1 analog comprising the following sequence:

trans-3-hexenoyl-NH-His-Ala-Glu- (SEQ. ID NO: 19)
Gly-Thr-Phe-Thr-Ser-Asp-Val-Ser-
Ser-Tyr-[(S)-Octylglycine]-Glu-
Gly-Gln-Ala-Ala-Lys-Leu-Phe-Ile-
Glu-Trp-Leu-Lys-Asn-NH$_2$.

In an embodiment, the present invention relates to a GLP-1 analog comprising the following sequence:

```
trans-3-hexenoyl-NH-His-Ala-Glu-   (SEQ. ID NO: 20)
Gly-Thr-Phe-Thr-Ser-Asp-Val-Ser-
Ser-Tyr-[(S)-Octylglycine]-Glu-
Gly-Gln-Ala-Ala-Lys-Leu-Phe-Ile-
Glu-Trp-Leu-Val-Lys-Asn-NH₂.
```

In an embodiment, the present invention relates to a GLP-1 analog comprising the following sequence:

```
His-Gly-Glu-Gly-Thr-Phe-Thr-Ser-   (SEQ. ID NO: 21)
Asp-Val-Ser-Ser-Tyr-[(S)-
Octylglycine]-Glu-Gly-Gln-Ala-
Ala-Lys-Leu-Phe-Ile-Glu-Trp-Leu-
Lys-Asn-NH₂.
```

In an embodiment, the present invention relates to a GLP-1 analog comprising the following sequence:

```
His-Gly-Glu-Gly-Thr-Phe-Thr-Ser-   (SEQ. ID NO: 22)
Asp-Val-Ser-Ser-[(S)-
Octylglycine]-Leu-Glu-Gly-Gln-
Ala-Ala-Lys-Ala-Phe-Ile-Glu-Trp-
Leu-Lys-Asn-NH₂.
```

In an embodiment, the present invention relates to a GLP-1 analog comprising the following sequence:

```
His-Ala-Glu-Gly-Thr-Phe-Thr-Ser-   (SEQ. ID NO: 23)
Asp-Val-Ser-Ser-Tyr-[(R)-
Octadecylglycine]-Glu-Gly-Gln-
Ala-Ala-Lys-Glu-Phe-Ile-Ala-
Trp-Leu-Val-Lys-Gly-Arg-NH₂.
```

The present invention also relates to the salt forms of the peptide analogs as described herein. The peptide analogs of the present invention are either sufficiently acidic or sufficiently basic to react with any of a number of inorganic bases or inorganic and organic acids to form a salt.

Acids commonly employed to form acid addition salts include inorganic acids such as but not limited to hydrochloric acid, hydrobromic acid, hydroiodic acid, sulfuric acid, phosphoric acid, and the like, as well as organic acids such as but not limited to p-toluenesulfonic acid, methanesulfonic acid, oxalic acid, p-bromophenylsulfonic acid, carbonic acid, succinic acid, citric acid, benzoic acid, acetic acid, and the like. Examples of such salts include the sulfate, pyrosulfate, bisulfate, sulfite, bisulfite, phosphate, chloride, bromide, iodide, acetate, propionate, decanoate, caprylate, formate, isobutyrate, caproate, heptanoate, propiolate, oxalate, malonate, succinate, suberate, sebacate, fumarate, maleate, phthalate, sulfonate, phenylacetate, phenylpropionate, phenylbutyrate, citrate, lactate, mandelate, glycolate, tartrate, methanesulfonate, propanesulfonate and the like.

Base addition salts include those derived from inorganic bases such as but not limited to ammonium, alkali or alkaline earth metal hydroxides, carbonates, bicarbonates, and the like. Such bases thus include sodium hydroxide, potassium hydroxide, ammonium hydroxide, potassium carbonate, and the like.

Salt forms of the peptide analogs as described herein are particularly preferred. It is understood that the peptide analogs of the present invention, when used for therapeutic purposes, may also be in the salt-form. The salt, however, must be pharmaceutically acceptable salt.

The present invention also relates to a composition comprising a therapeutically effective amount of a peptide as described herein, or a pharmaceutically acceptable salt thereof, in association with at least one constituent selected from the group consisting of pharmaceutically acceptable carriers, diluents and excipients. In a particular embodiment, the present invention relates to a composition comprising a therapeutically effective amount of a peptide as described herein, or a pharmaceutically acceptable salt thereof, wherein the therapeutically effective amount is ranging from about 1 mcg to about 10 mg.

The present invention also relates to a composition comprising a prophylactically effective amount of a peptide as described herein, or a pharmaceutically acceptable salt thereof, in association with at least one constituent selected from the group consisting of pharmaceutically acceptable carriers, diluents and excipients.

The present invention further relates to a method of treating a disease or condition associated with a disorder of glucose metabolism. Moreover, the present invention relates to a method of preventing (e.q. prophylaxis) a disease or condition associated with a disorder of glucose metabolism. Non-limiting examples of glucose disorders include: diabetes mellitus of Type I or Type II, insulin resistance, as well as weight disorders and diseases or conditions associated therewith. Non-limiting examples of weight disorders or associated conditions include obesity, overweight-associated conditions, satiety deregulation, reduced plasma insulin levels, increased blood glucose levels, and reduced pancreatic beta cell mass.

In an embodiment, the present invention relates to a method for treating diabetes mellitus of Type I or Type II, comprising administering to a subject in need of such treatment a therapeutically effective amount of a peptide as described herein, or a pharmaceutically acceptable salt thereof.

In an embodiment, the present invention relates to a method for treating insulin resistance, comprising administering to a subject in need of such treatment a therapeutically effective amount of a peptide as described herein, or a pharmaceutically acceptable salt thereof.

In an embodiment, the present invention relates to a method for weight lowering of a subject, comprising administering to a subject in need of weight lowering an effective amount of a peptide as described herein, or a pharmaceutically acceptable salt thereof.

In an embodiment, the present invention relates to a method for reducing satiety of a subject, comprising administering a therapeutically effective amount of a peptide as described herein, or a pharmaceutically acceptable salt thereof, to a subject in need thereof.

In an embodiment, the present invention relates to a method for post-prandially increasing plasma insulin levels in a subject, comprising administering a therapeutically effective amount of a peptide as described herein, or a pharmaceutically acceptable salt thereof, to a subject in need thereof.

In an embodiment, the present invention relates to a method for reducing fasting blood glucose levels in a subject, comprising administering a therapeutically effective amount of a peptide as described herein, or a pharmaceutically acceptable salt thereof, to a subject in need thereof.

In an embodiment, the present invention relates to a method for increasing pancreatic beta cell mass in a subject, comprising administering a therapeutically effective amount of a peptide as described herein, or a pharmaceutically acceptable salt thereof, to a subject in need thereof.

In yet another embodiment, the present invention relates to methods for administering the peptides, or pharmaceutically acceptable salts thereof, as described herein. Non-limiting examples of methods for administering the peptides, or pharmaceutically acceptable salts thereof, include subcutaneous, intravenous, transdermal, oral, bucal, and intranasal.

In a further embodiment, the present invention relates to a use of the peptides as described herein, or pharmaceutically acceptable salts thereof, for treating diabetes mellitus of Type I or Type II in a subject.

In a further embodiment, the present invention relates to a use of the peptides as described herein, or pharmaceutically acceptable salts thereof, for treating insulin resistance in a subject.

In a further embodiment, the present invention relates to a use of the peptides as described herein, or pharmaceutically acceptable salts thereof, for lowering weight of a subject.

In a further embodiment, the present invention relates to a use of the peptides as described herein, or pharmaceutically acceptable salts thereof, for reducing satiety of a subject.

In a further embodiment, the present invention relates to a use of the peptides as described herein, or pharmaceutically acceptable salts thereof, for post-prandially increasing plasma insulin levels in a subject.

In a further embodiment, the present invention relates to a use of the peptides as described herein, or pharmaceutically acceptable salts thereof, for reducing fasting blood glucose levels in a subject.

In a further embodiment, the present invention relates to a use of the peptides as described herein, or pharmaceutically acceptable salts thereof, for increasing pancreatic beta cell mass in a subject.

In a further embodiment, the present invention relates to a use of the peptides as described herein, or pharmaceutically acceptable salts thereof, for preparing a medicament for treating diabetes mellitus of Type I or Type II in a subject.

In a further embodiment, the present invention relates to a use of the peptides as described herein, or pharmaceutically acceptable salts thereof, for preparing a medicament for treating insulin resistance in a subject.

In a further embodiment, the present invention relates to a use of the peptides as described herein, or pharmaceutically acceptable salts thereof, for preparing a medicament for weight lowering of a subject.

In a further embodiment, the present invention relates to a use of the peptides as described herein, or pharmaceutically acceptable salts thereof, for preparing a medicament for increasing satiety of a subject.

In a further embodiment, the present invention relates to a use of the peptides as described herein, or pharmaceutically acceptable salts thereof, for preparing a medicament for post-prandially increasing plasma insulin levels in a subject.

In a further embodiment, the present invention relates to a use of the peptides as described herein, or pharmaceutically acceptable salts thereof, for preparing a medicament for reducing fasting blood glucose levels in a subject.

In yet a further embodiment, the present invention relates to a use of the peptides as described herein, or pharmaceutically acceptable salts thereof, for preparing a medicament for increasing pancreatic beta cell mass in a subject.

The present invention is further illustrated by the following non-limiting examples.

EXAMPLE 1

Solid Phase Synthesis of GLP-1 Analogs and Coupling of an R1 Moiety at His7

The peptide analogs of the present invention are prepared employing standard automated and/or manual solid phase peptide synthesis techniques, using fluorenylmethoxycarbonyl-protected α-amino acids having appropriate side-chain protection and using a BHA resin. After completion of the synthesis, the peptide analogs are cleaved from the solid phase support with simultaneous side-chain deprotection. Optionally, salicylic acid or trans-3-hexenoic acid was coupled to the N-terminus of His7 using the same methods as used for amino acid coupling. The crude peptides were further purified by preparative HPLC, followed by vacuum-drying and lyophilizing. The peptide purity was assessed by analytical HPLC and the peptide masses were determined by MALDI-TOF MS analysis. The peptides were prepared as TFA salts and dissolved in 20 mM acetic acid for administration to animals. Representative examples of GLP-1 analogs are illustrated below in Table 2.

TABLE 2

Representative GLP-1 analogs

| Peptide Number | SEQ ID NO: | Sequence[1] |
|---|---|---|
| TH0318 | 39 | 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ |
| TH0322 | 27 | His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Gly-Arg-NH$_2$ |
| TH0323 | 40 | His-Ala-Glu-Gly-Thr-[(S)-Octylglycine]-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ |
| TH0324 | 24 | His-Ala-Glu-Gly-Thr-[(L)-Bip]-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ |
| TH0367 | 42 | 2-Hydroxybenzoyl-NH-His-Ala-Glu-Gly-Thr-Phe-Thr-Ser-Asp-Val-Ser-Lys-Gln-Leu-Glu-Glu-Gln-Ala-Ala-Lys-Glu-Phe-Ile-Ala-Trp-Leu-Val-Lys-Gly-Arg-NH$_2$ |
| TH0368 | 31 | 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-Gly-NH$_2$ |
| TH0369 | 43 | 2-Hydroxybenzoyl-NH-His-Ala-Glu-Gly-Thr-Phe-Thr-Ser-Asp-Val-Ser-Lys-Gln-Leu-Glu-Glu-Gln-Ala-Ala-Lys-Leu-Phe-Ile-Glu-Trp-Leu-Lys-Asn-Gly-NH$_2$ |

TABLE 2-continued

Representative GLP-1 analogs

| Peptide Number | SEQ ID NO: | Sequence[1] |
|---|---|---|
| TH0370 | 44 | 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-NH$_2$ |
| TH0371 | 45 | 2-Hydroxybenzoyl-NH-His-Ala-Glu-Gly-Thr-Phe-Thr-Ser-Asp-Val-Ser-Lys-Tyr-Leu-Glu-Glu-Gln-Ala-Ala-Lys-Ala-Phe-Ile-Glu-Trp-Leu-Lys-Asn-Aib-NH$_2$ |
| TH0372 | 46 | 2-Hydroxybenzoyl-NH-His-Ala-Glu-Gly-Thr-Phe-Thr-Ser-Asp-Val-Ser-Lys-Tyr-Leu-Ala-Glu-Gln-Ala-Ala-Lys-Ala-Phe-Ile-Glu-Trp-Leu-Lys-Asn-NH$_2$ |
| TH0373 | 47 | 2-Hydroxybenzoyl-NH-His-Ala-Glu-Gly-Thr-Phe-Thr-Ser-Asp-Val-Ser-Ser-Tyr-Leu-Glu-Ala-Gln-Ala-Ala-Lys-Glu-Phe-Ile-Gln-Trp-Leu-Val-Lys-Gly-NH$_2$ |
| TH0384 | 19 | His-Gly-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Lys-Asn-NH$_2$ |
| TH0385 | 16 | His-Gly-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Val-Lys-Asn-NH$_2$ |
| TH0392 | 28 | His-Gly-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Gly-Arg-NH$_2$ |
| TH0393 | 37 | His-Gly-Glu-Gly-Thr-Phe-Thr-Ser-Asp-Val-Ser-Ser-[(S)-Octylglycine]-Leu-Glu-Gly-Gln-Ala-Ala-Lys-Ala-Phe-Ile-Glu-Trp-Leu-Lys-Asn-NH$_2$ |
| TH0395 | 22 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Ala-Phe-Ile-Glu-Trp-Leu-Lys-Asn-NH$_2$ |
| TH0396 | 26 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Ala-Phe-Ile-Glu-Trp-Leu-Val-Lys-Asn-NH$_2$ |
| TH0397 | 20 | His-Gly-Glu-Gly-Thr-Phe-Thr-Ser-Asp-Val-Ser-Ser-Tyr-[(S)-Octylglycine]-Glu-Gly-Gln-Ala-Ala-Lys-Ala-Phe-Ile-Glu-Trp-Leu-Lys-Asn-NH$_2$ |
| TH0398 | 24 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Lys-Asn-NH$_2$ |
| TH0399 | 25 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Val-Lys-Asn-NH$_2$ |
| TH0415 | 48 | trans-3-hexenoyl-NH-His-Ala-Glu-Gly-Thr-Phe-Thr-Ser-Asp-Val-Ser-Ser-Tyr-Leu-Gln-Gly-Gln-Ala-Ala-Lys-Ala-Phe-Ile-Glu-Trp-Leu-Lys-Asn-NH$_2$ |
| TH0420 | 49 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Lys-Asn-NH$_2$ |
| TH0421 | 50 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Arg-Glu-Phe-Ile-Ala-Trp-Leu-Val-Lys-Gly-Arg-NH$_2$ |
| TH0422 | 51 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Gln-Trp-Leu-Val-Lys-Gly-Arg-NH$_2$ |
| TH0423 | 52 | His-Gly-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-[(S)-Octylglycine]-NH$_2$ |
| TH0424 | 29 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Gly-Arg-NH$_2$ |
| TH0425 | 53 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-[(S)-Octylglycine]-Phe-Ile-Ala-Trp-Leu-Val-Lys-Gly-Arg-NH$_2$ |
| TH0426 | 30 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Aib-Arg-NH$_2$ |
| | 32 | His-Gly-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-NH$_2$ |
| | 33 | His-Gly-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Val-Lys-Asn-NH$_2$ |
| | 34 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Lys-Asn-NH$_2$ |
| | 34 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Lys-Asn-CONH$_2$ |
| | 35 | trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Vat-Lys-Asn-NH$_2$ |
| | 36 | His-Gly-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Lys-Asn-NH$_2$ |
| | 17 | 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-NH$_2$ |

TABLE 2-continued

Representative GLP-1 analogs

| Peptide Number | SEQ ID NO: | Sequence[1] |
|---|---|---|
| | 18 | 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Lys-Asn-Aib-$NH_2$ |
| | 21 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-$NH_2$ |
| | 23 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Val-Lys-Asn-$NH_2$ |
| TH0429 | 54 | trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Aib-Arg-$NH_2$ |
| TH0430 | 55 | His-Ala-Glu-Gly-Thr-Phe-Thr-Ser-Asp-Val-Ser-Ser-Tyr-Aib-Glu-Gly-Gln-Ala-Ala-Lys-Glu-Phe-Ile-Ala-Trp-Leu-Val-Lys-Gly-Arg-$NH_2$ |
| TH0443 | 56 | His-Ala-Glu-Gly-Thr-Phe-Thr-Ser-Asp-Val-Ser-Ser-Tyr-[(R)-Octylglycine]-Glu-Gly-Gln-Ala-Ala-Lys-Glu-Phe-Ile-Ala-Trp-Leu-Val-Lys-Gly-Arg-$NH_2$ |
| TH0455 | 57 | His-Ala-Glu-Gly-Thr-Phe-Thr-Ser-Asp-Val-Ser-Ser-Tyr-Nle-Glu-Gly-Gln-Ala-Ala-Lys-Glu-Phe-Ile-Ala-Trp-Leu-Val-Lys-Gly-Arg-$NH_2$ |
| TH0494A | 38 | His-Ala-Glu-Gly-Thr-Phe-Thr-Ser-Asp-Val-Ser-Ser-Tyr-[(R)-Octadecylglycine]-Glu-Gly-Gln-Ala-Ala-Lys-Glu-Phe-Ile-Ala-Trp-Leu-Val-Lys-Gly-Arg-$NH_2$ |
| TH0494B | 58 | His-Ala-Glu-Gly-Thr-Phe-Thr-Ser-Asp-Val-Ser-Ser-Tyr-[(S)-Octadecylglycine]-Glu-Gly-Gln-Ala-Ala-Lys-Glu-Phe-Ile-Ala-Trp-Leu-Val-Lys-Gly-Arg-$NH_2$ |

[1]L-Bip: L-biphenylalanine; Aib: Aminoisobutyric acid; Nle: Norleucine

EXAMPLE 2

Effect of GLP-1 Analogs on Post-Prandial Blood Glucose Levels in CD-1 Mice

Overnight fasted CD-1 normal female mice (6 wk. Charles River, Montreal, Canada), were fed ad libidum for 30 minutes. GLP-1 peptides (100-400 μg/kg) were injected sc at 30 minutes. Blood samples were drawn by tail vein excision and blood glucose levels (mmol/L) were determined for the next 6 hours using a One-Touch™ glucometer. The "Area Under the Curve" (AUC Glucose [mmol/L/120 min]) was calculated using the trapezoidal method.

As shown in FIG. 1, native GLP-1 and the DPPIV resistant analogue of GLP-1 [2-hydroxybenzoyl-GLP-1(7-36)$NH_2$ (TH0318)] displayed hypoglycemic action for 2 hours, whereas the modified analogs TH0322 and TH0368 produced prolongation of hypoglycemia for at least 4 hours, similar to Exendin-4™.

EXAMPLE 3

Effect of GLP-1 Analogs on Blood Glucose Levels in Hypoglycemic Sprague-Dawley Rats The animals (Sprague-Dawley rats) were maintained on standard laboratory chow under a 12:12 light:dark cycle. Following a 12 hour fasting period, the animals were anesthetized (Isoflurane 2%) and a carotid and jugular catheter installed to allow blood withdrawal and glucose injections (1.0 g/kg bolus followed by an infusion of 1.4 g/kg/hr) respectively. The animals received a subcutaneous injection of the analogs at different concentrations (300 μg/kg) 90 minutes after initiating the glucose bolus and infusion, at a time period where blood glucose concentrations have reached a steady level. Blood glucose measurements were taken prior to and 30, 60, 90, 100, 110, 120, 135, 150, 180, 210, and sometimes 240 and 300 minutes after the injection of glucose.

Glucose measurements were carried out immediately following sampling (0.3-0.4 ml; if needed) by placing a blood droplet on a glucometer strip. The glucose measurements were carried out prior to plasma separation (centrifugation) required to perform the insulin and/or any other assay.

Figure 2:
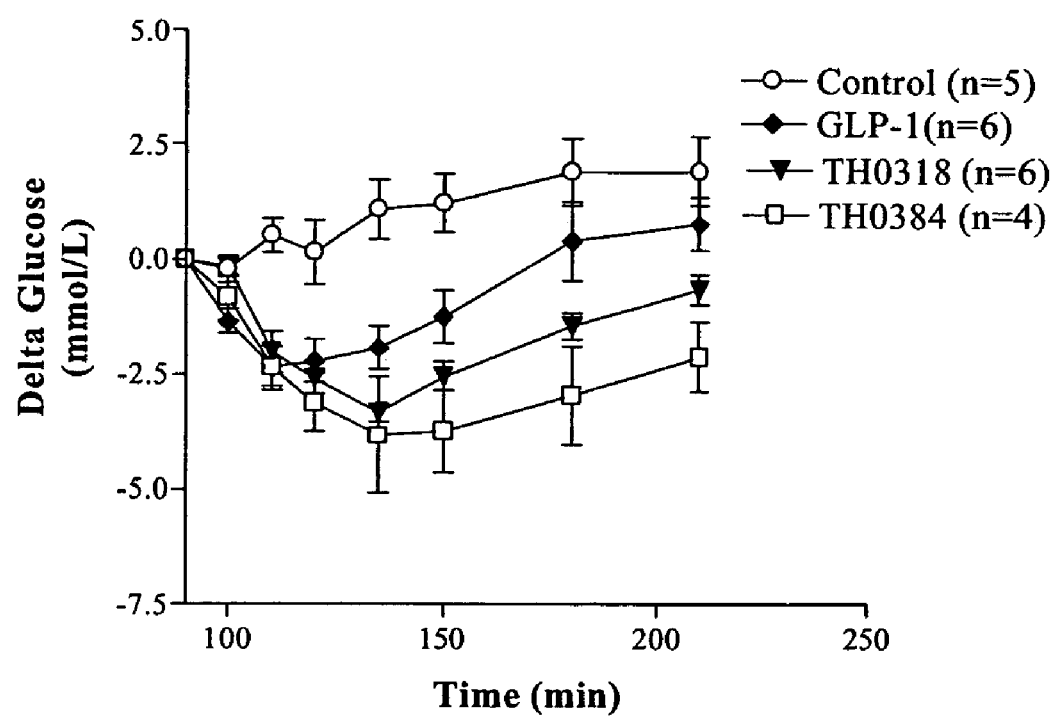
FIG. 2 shows blood glucose levels in Sprague-Dawley rats that were subjected to hyperglycemic clamping at 15 mM. Various peptides, including peptides of the present invention (100 μg/kg) were administered sc. Alterations in blood glucose levels (Delta glucose: mM) are shown on the abscissa. The data are presented as mean ±SEM values.

As shown in FIG. 2, the GLP-1 analog TH0384 was found to be more potent than GLP-1 or the 2-hydroxybenzoyl-GLP-1 analog TH0318.

EXAMPLE 4

Displacement of $^{125}$I-GLP-1(7-36)$NH_2$ with GLP-1 Analogs Using RINm5F Cells RINm5F cells (ATCC # CRL-2058) were grown according to the manufacturer's specifications. Cells from confluent flasks were maintained for four (4) days prior to the experiment. The cells were then scrapped and collected in 15 ml conical tubes followed by sonication and evaluation of protein levels. The cell membranes were diluted to obtain aliquots of 400 μg of protein per assay tube.

Aliquots of RINm5F cells containing 400 μg of protein were incubated at 22° C. (room temperature) for 45 minutes in glass tubes containing 100 μl of sodium phosphate buffer (10 mM, pH 7.4) comprising 100 mM NaCl, 2 mM $MgCl_2$, mini protease inhibitor cocktail (1 tablet per 100 ml, Roche diagnostics GmbH) and varying concentrations of GLP-1 analogs ($10^{-10}$ to $10^{-5}$) in the presence of 100000 cpm of $I^{125}$GLP-1(7-36)$NH_2$ (3 nM). The reactions were stopped using 100 mM Tris-HCl (3×3 mL, pH 7.4) and the solutions passed through a GF/C Whatman glass microfiber filter. The latter was subsequently placed into glass tubes and counted on a Packard COBRA II Gamma counter™. Displacement isotherms were traced and analyzed using Prism™ (Graph-Pad, Ca).

Figure 3:
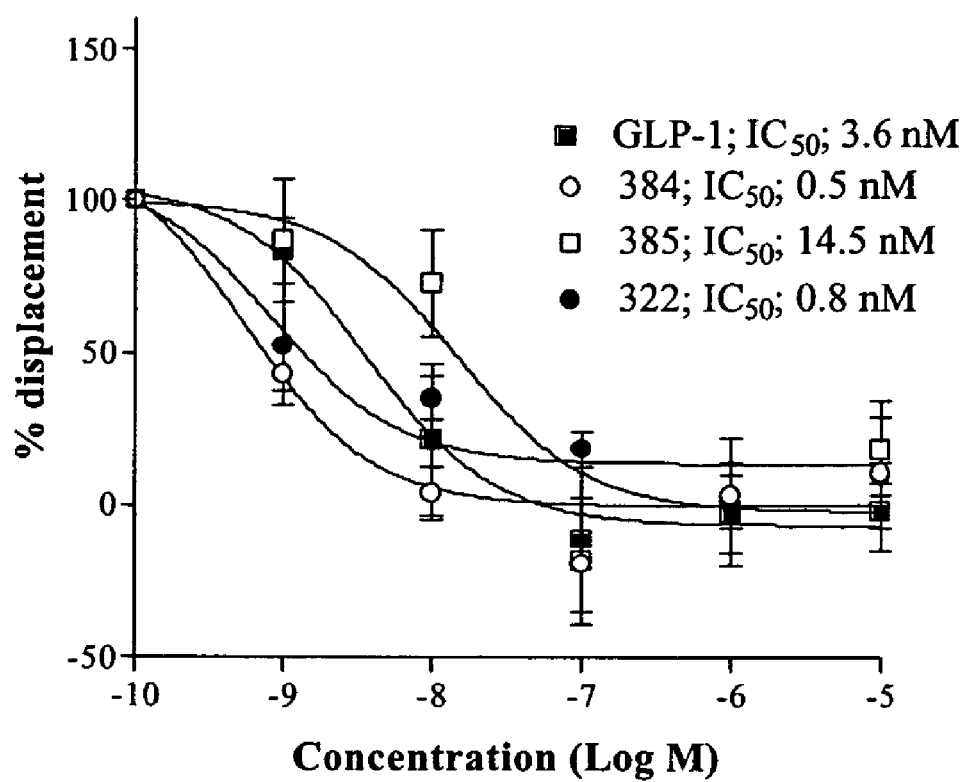
FIG. 3 shows the % displacement of $^{125}$I-GLP-1(7-36)NH$_2$ by the GLP-1 analogs of the present invention. The IC$_{50}$ is calculated as the half-maximal inhibition of binding of the radiolabeled peptide.

As shown in FIG. 3, the GLP-1 analogs TH0322 and TH0384 were considerably more potent than GLP-1 in displacing receptor bound ligand in Rinm5F cells.

EXAMPLE 5

Effect on the In-Vitro Secretion of cAMP in Response to GLP-1 and Analogs Using RINm5F Cells RINm5F cells (ATCC # CRL-2058) were grown according to the manufacturer's specifications. Cells from approximately 90% confluent flasks were trypsinized and counted. The cells were then seeded in a 96-well plate (Clear Sarstedt plate™ with a clear flat bottom) with media (RPMI 1640, 10% FBS, 2 mM Glutamine, 0.5% Pen-Strep; 100 µl) and assayed 4 days after reaching confluency.

Stock solutions of GLP-1 and analogs were prepared using 20 mM acetic acid at a concentration of 1 mg/ml. Samples of the stock solutions were then aliquoted in 100 µl volumes (100 µg), to which were then added 400 µl $H_2O$. The aliquots were then frozen and lyophilized overnight. The lyophilized samples were kept at −80° C. until used. The samples were prepared just prior to running the experiments, at a concentration of 1 mM (accounting for peptide purity and peptide content when available). From 2× stock solutions, dose-responses ($10^{-10}$ M to $10^{-5}$ M) were measured in RPMI containing 0.1 mM IBMX. GLP-1 dilutions were prepared less than 30 minutes before the beginning the assay.

Cell culture media was gently aspirated from the wells. The cells were then pre-incubated in 100 µl RPMI 0.1 mM IBMX at 37° C. for 10 minutes. Following pre-incubation, 100 µl of each 2× GLP-1 dilution was added to the wells in triplicate and incubated at 37° C. for 30 minutes. At the end of the incubation period, the supernatant was collected and assayed for cAMP concentration, using a radioimmunoassay kit (DPC). Radioactive counts were transformed into cAMP amounts using a standard curve. The obtained cAMP values were corrected for the total protein in the corresponding wells as determined using the Coomassie blue assay. The cAMP values are expressed as mean ±SEM in pmol/mg protein (Table 3). Dose responses of cAMP were fitted to a sigmoidal curve model (fixed slope) using GraphPad Prism 3.02™.

When performing a protein assay, the amount of protein per well is assayed for each sample. The cells were lysed with NaOH (0.1 N) and a 10 µl aliquot was used to assay the protein levels. This is done using Coomassie Blue (Pierce) and an automated plate reader Emax Pro™ (Molecular Devices).

TABLE 3

Effects of GLP-1 and GLP-1 analogs on cAMP production in RINm5F cells.

| GLP-1 analog | $EC_{50}$ (nM) | Maximal response (pmol/mg protein) | n |
| --- | --- | --- | --- |
| GLP-1 | 1.8 ± 0.9 | 1.5 ± 0.3 | 3 |
| TH0318 | 13.6 ± 2.9 | 3.5 ± 0.2 | 5 |
| TH0322 | 0.2 ± 0.2 | 1.0 ± 0.2 | 3 |
| TH0424 | 6.3 ± 1.7 | 4.3 ± 0.2 | 4 |
| TH0426 | 0.4 ± 0.4 | 5.7 ± 0.6 | 2 |
| TH0395 | 6.1 ± 0.9 | 3.7 ± 0.4 | 4 |
| TH0396 | 2.3 ± 1.7 | 3.9 ± 0.3 | 4 |

Mean ± SEM;
n = number of dose-response curves done in triplicate.

EXAMPLE 6

Post-Prandial Glucose Lowering Effects of GLP-1 Analogs in Fed CD-1 Mice

The animals (CD-1 mice) were maintained on standard laboratory chow under a 12:12 light:dark cycle. The animals were kept in groups of 4 mice per cage. Following a 12 hour fasting period (water was provided ad libidum), the animals were presented food for a period of 30 minutes. The amount of food eaten was monitored. The food was then removed and the animals were injected subcutaneously with either vehicle or with a GLP-1 analogue to be tested. The glucose levels were measured throughout the experiment at time −30 minutes, 0, 30, 60, 120, 180, 240, 300 and 360 minutes.

A small piece of the tip of the tail of the CD-1 mice was cut with a scalpel and a drop of blood drawn by applying light pressure with the thumb and index from the base of the tail to the tip. The drop of blood was placed on a glucometer strip (Accucheck™ compact, Roche) and a reading obtained. The scab was removed and the same procedure applied for each subsequent measurement.

Figure 4:
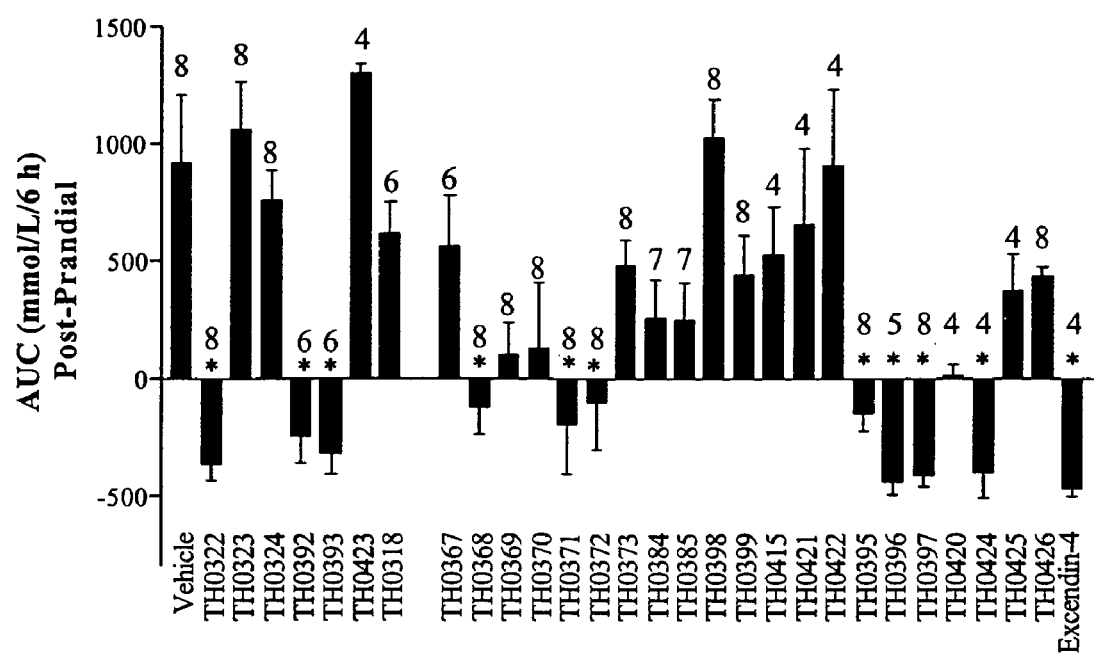
FIG. 4 shows the effect on post-prandial glucose levels in CD-1 mice. The animals were fasted overnight and then allowed to eat for a period of 30 minutes. Immediately following feeding, the animals received a subcutaneous injection of vehicle (20 mM acetic acid), GLP-1 analogs (400 μg/kg) and Exendin-4™ (40 μg/kg). Post-prandial AUC glucose levels for a 6 hour period are presented as a bar (mean ±SEM; n=the number of animals as presented above the bar). The average fasting glucose level was measured as being 4.11±0.07 mmol/L (n=189), corresponding to a fasting AUC of 1615±29.7 mmol/L/6 h which was subtracted from all data, giving a net post-prandial glucose level. *P<0.05 vs Vehicle by ANOVA.
Figure 5:
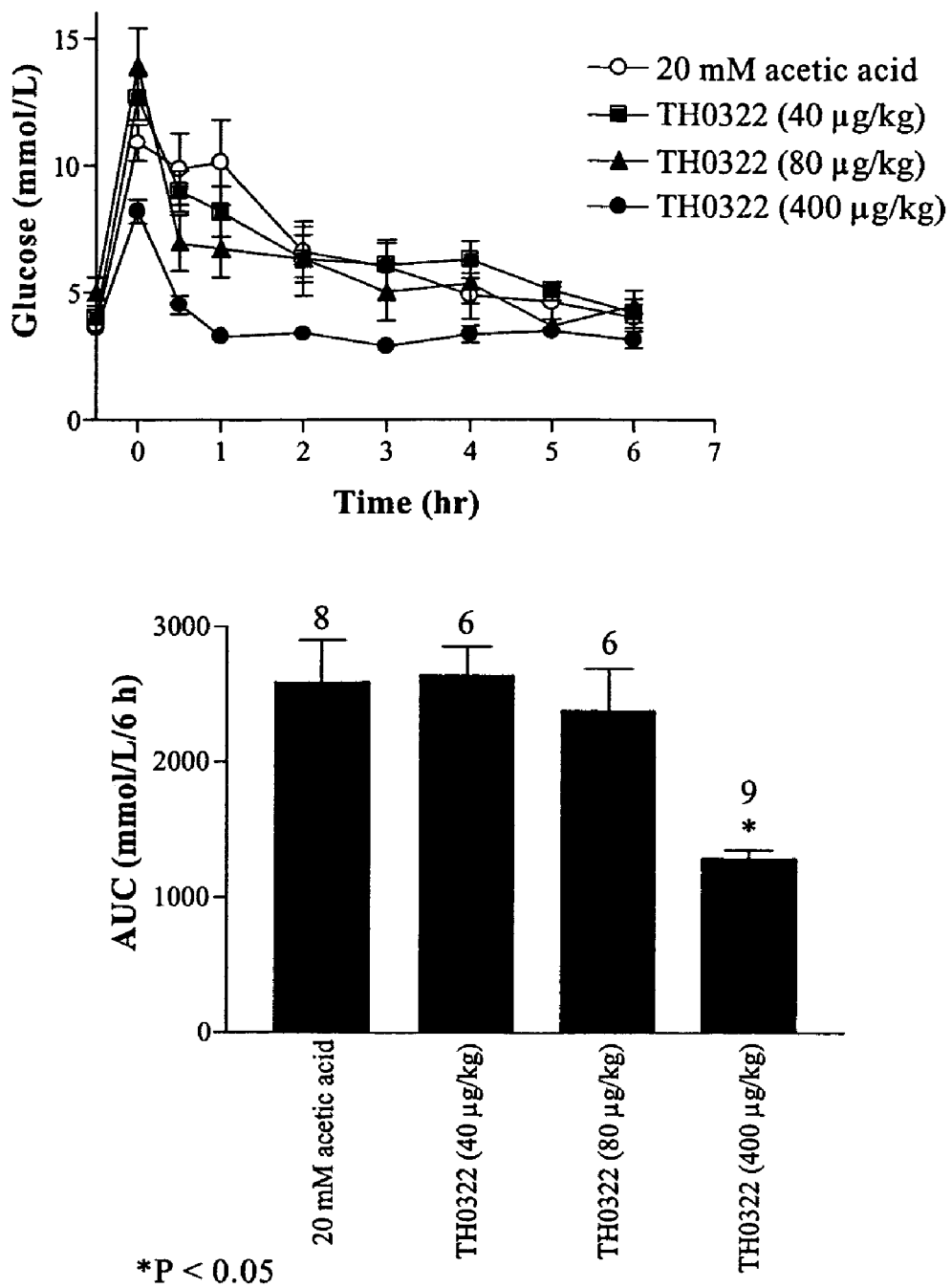
FIGS. 5, 6, 7 and 8 illustrate the effect (dose response) on post-prandial glucose levels in CD-1 mice for selected analogs. CD-1 mice were fasted overnight and then allowed to eat for a period of 30 minutes. Following feeding, the animals received a subcutaneous injection of vehicle (20 mM acetic acid) or different doses of GLP-1 analogs (dose response from 40-400 μg/kg). The blood glucose levels were measured for a period of up to 6 hours following injection (mean ±SEM; upper panel). The AUC glucose for the 6 hours period is presented as a bar (mean ±SEM; lower panel; n is the number of animals as presented on top of the lower panel bars)
Figure 6:
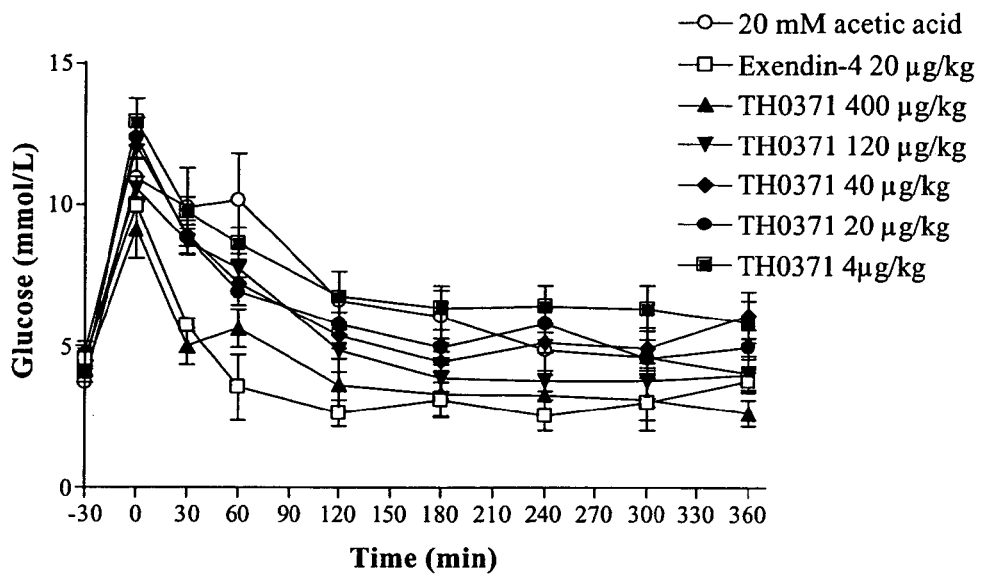
Figure 6:
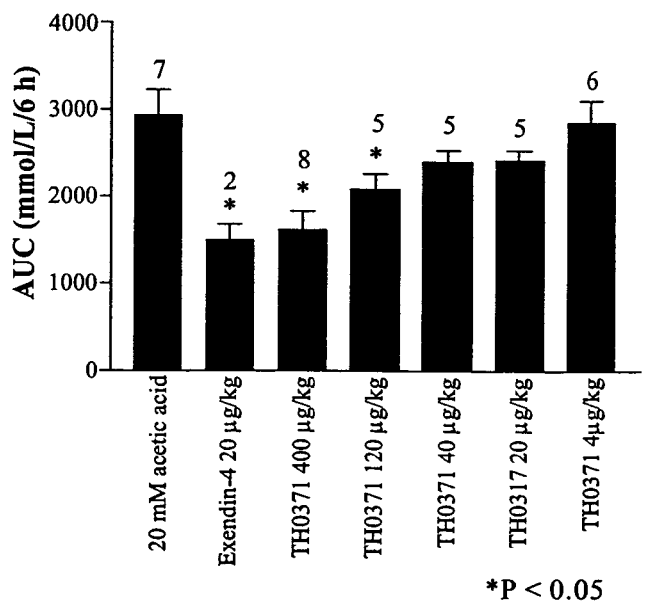
Figure 7:
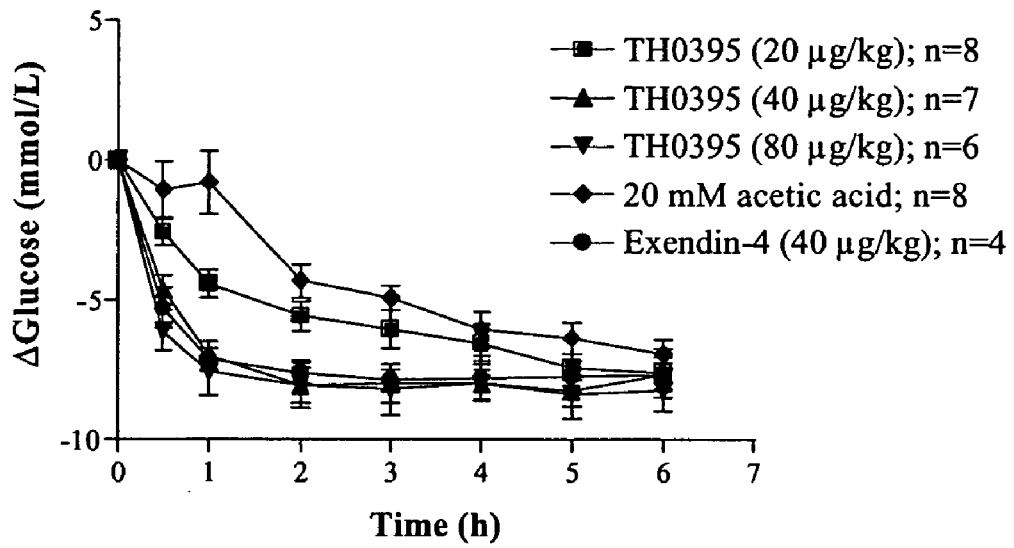
Figure 7:
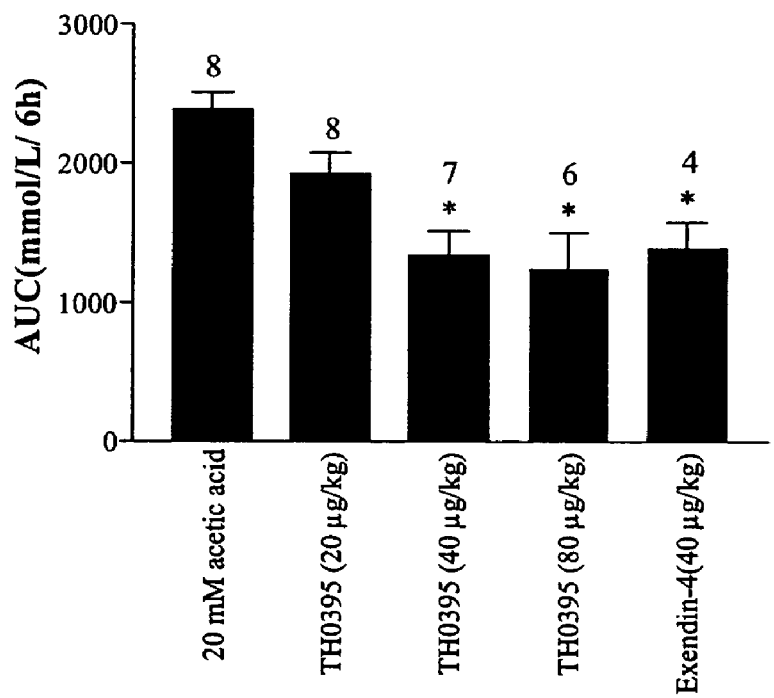
Figure 8:
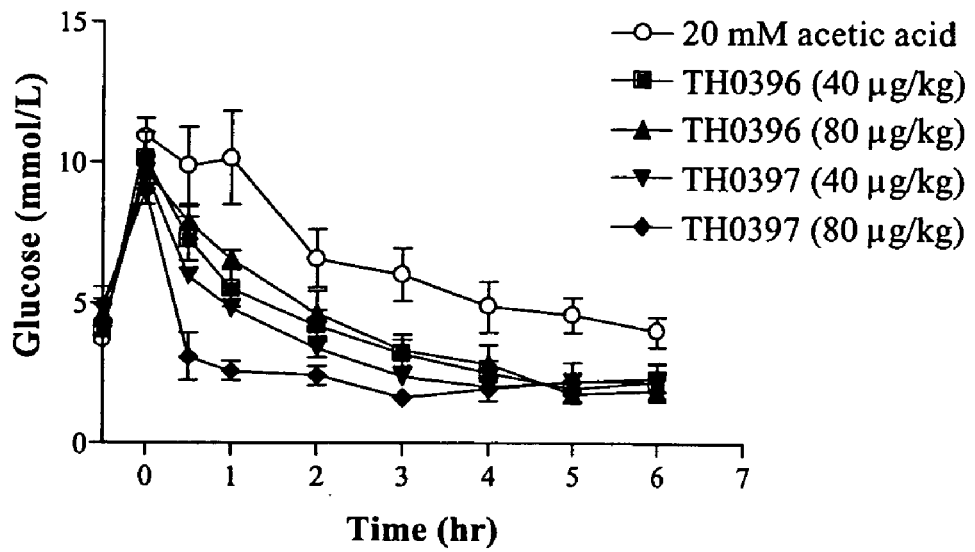
Figure 8:
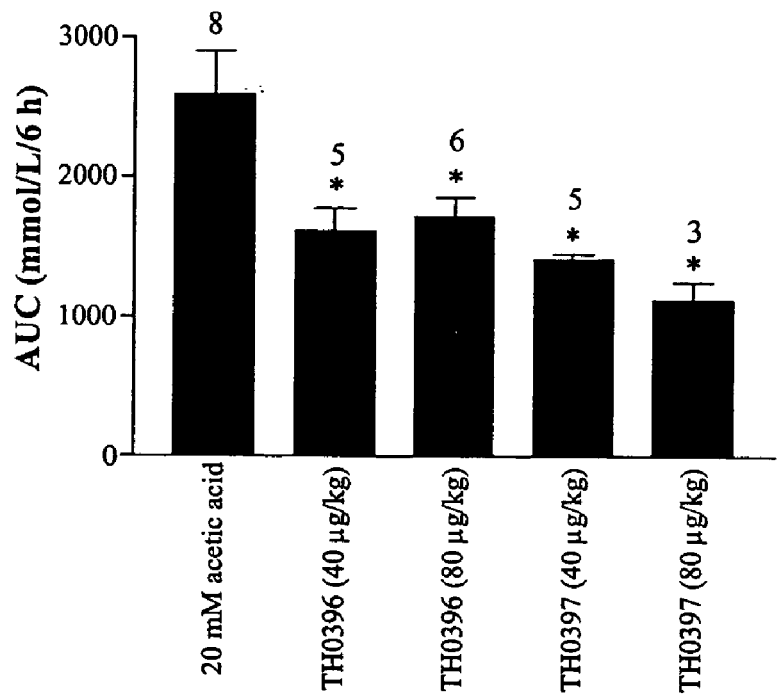
Figure 9:
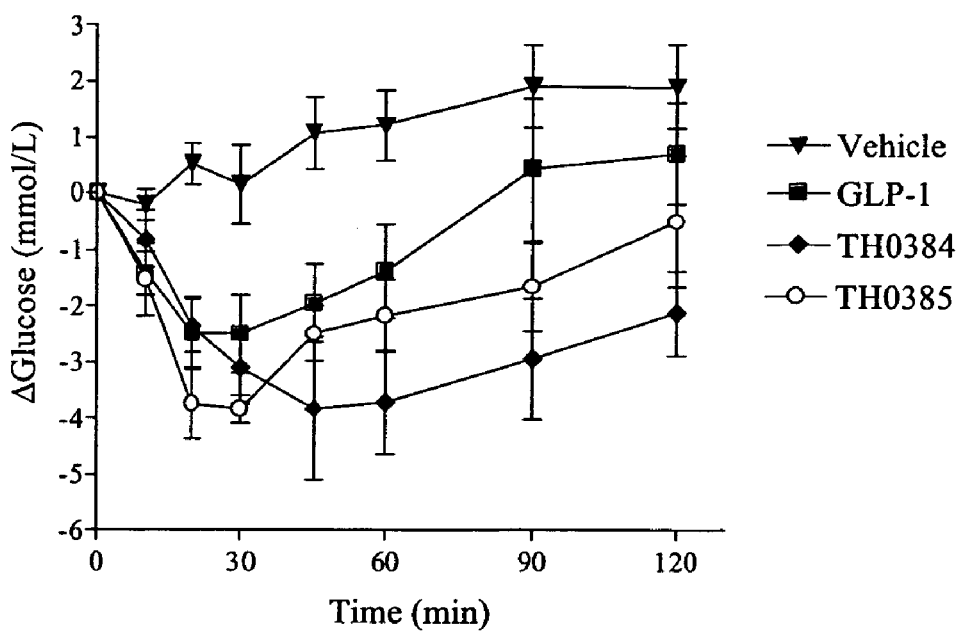
FIGS. 9 and 10 illustrate the evaluation of blood glucose clearance in clamped-glucose (15 mmol/L) Sprague-Dawley rats. The Sprague-Dawley rats were kept on a 12:12 light:dark cycle and fasted 12 hours (overnight) prior to the experiment. The delta glucose was obtained starting 90 minutes after initiating glucose infusion in the animal, at a time when the blood glucose levels have reached a steady level, at which point the animals received a subcutaneous injection of vehicle, GLP-1 or GLP-1 analogue (300 μg/kg for GLP-1, TH0384 and TH0385; 100 μg/kg for TH0395, TH0396, TH0424 and TH0426). The data are mean ±SEM; n is the number of animals as presented on top of the lower panel bars.
Figure 9:
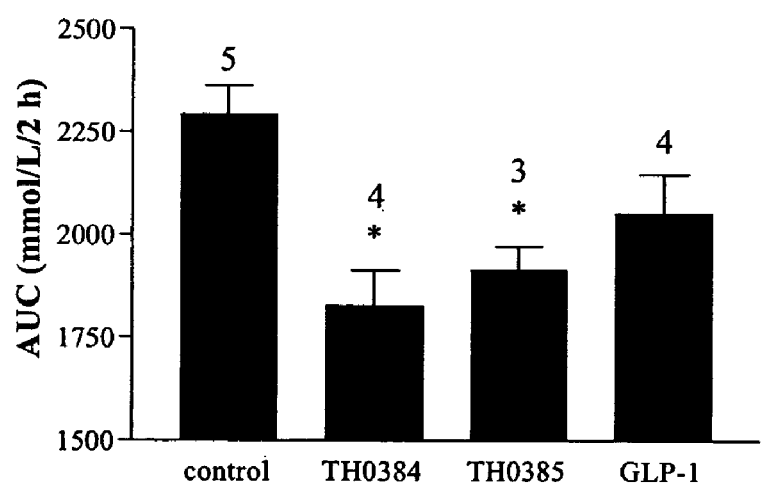

As shown in FIG. 4, the GLP-1 analogs TH0395, TH0396, TH0397 and TH0424 were found to potently reduce postprandial glucose in the fed CD-1 mice.

EXAMPLE 7

Glucose Lowering Effects of GLP-1 Analogs in the Clamped Sprague-Dawley Rat Model The animals (Sprague-Dawley rats) were maintained on standard laboratory chow under a 12:12 light:dark cycle. Following a 12 hours fasting period, the animals were fed for 10 minutes ad then anesthetized (Isoflurane 2%). A carotid and jugular catheter were installed to allow blood withdrawal and glucose injections (1.0 g/kg bolus followed by an infusion of 1.4 g/kg/hr) respectively. The animals received a subcutaneous injection of the analogue tested (300 µg/kg) 90 minutes after initiating the glucose bolus and infusion; at a time period when blood glucose concentrations reached a steady level. Blood glucose measurements were taken prior to and 30, 60, 90, 100, 110, 120, 135, 150, 180, 210, and sometimes 240 and 300 minutes after beginning the glucose infusion.

In all the methods used, glucose measurements were performed immediately after sampling (0.3-0.4 ml; if needed). A drop of blood was placed on a glucometer strip (Accucheck™ compact, Roche) and a reading obtained prior to the plasma separation (centrifugation) needed to perform the insulin or any other assay.

Figure 10:
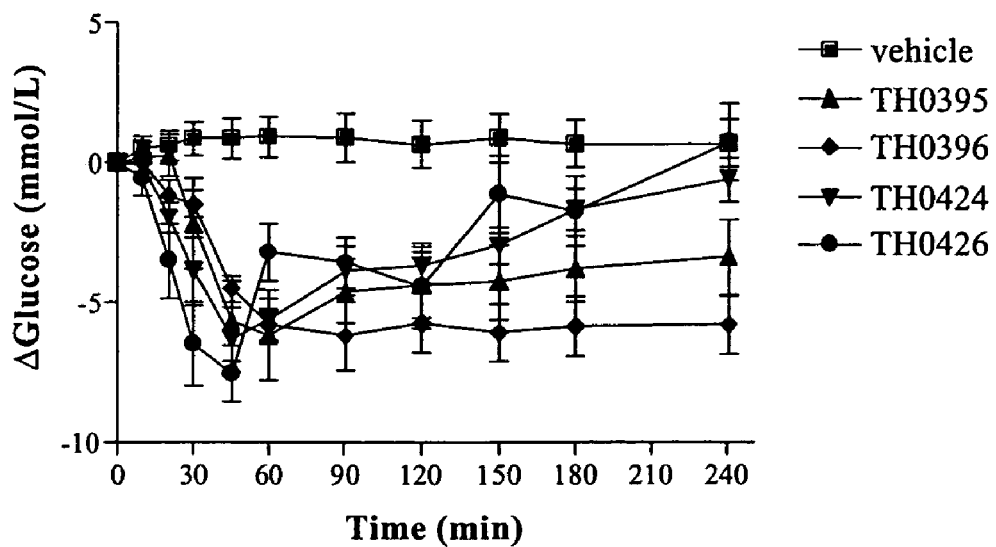
Figure 10:
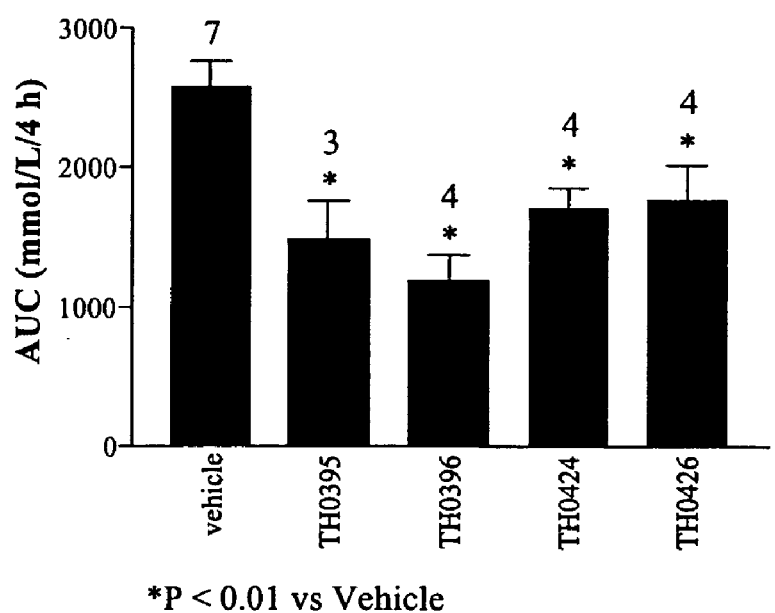
Figure 11:
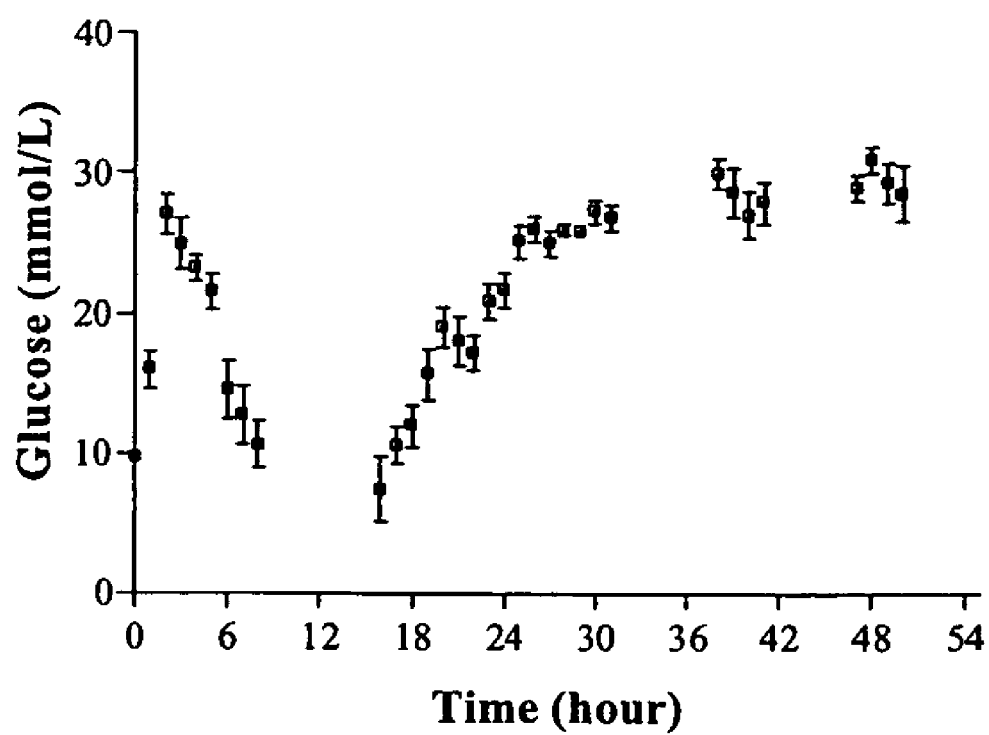
FIG. 11 illustrates the development of a hyperglycemic profile in CD-1 mice injected with Streptozotocin. The CD-1 mice were fed ad libidum for the duration of the experiment, were kept on a 12:12 light:dark cycle and were monitored for a total of 50 hours. Two groups were administered Streptozocin (400 μg/kg) to allow some time overlap and given a glucose profile as complete as possible. Blood glucose was measured using a portable glucometer to assess the time-dependent development of hyperglycemia in this diabetic model (mean ±SEM; n=8 at each time point).
Figure 12:
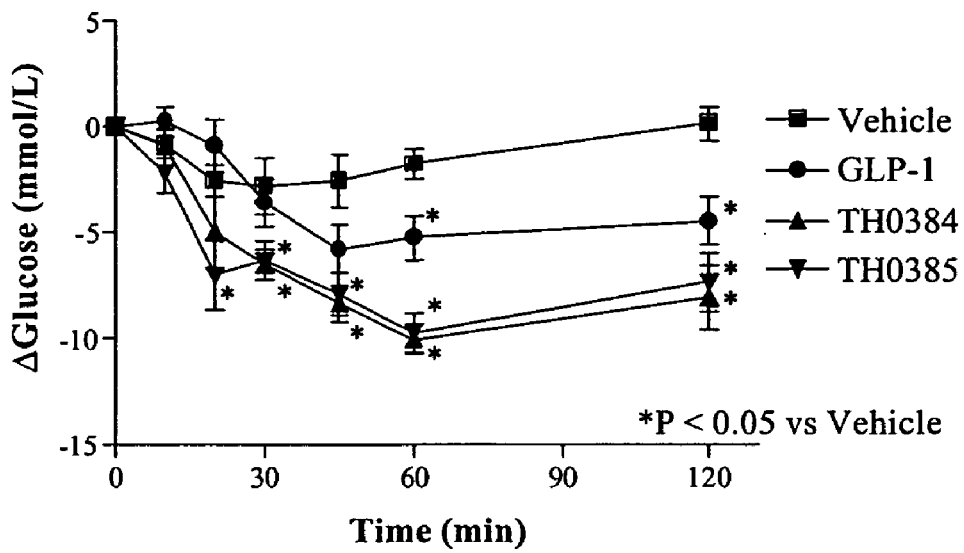
FIGS. 12, 13, and 14 illustrate the effects of GLP-1 analogs on the glucose profile in fed STZ-induced diabetic CD-1 mice.
Figure 12:
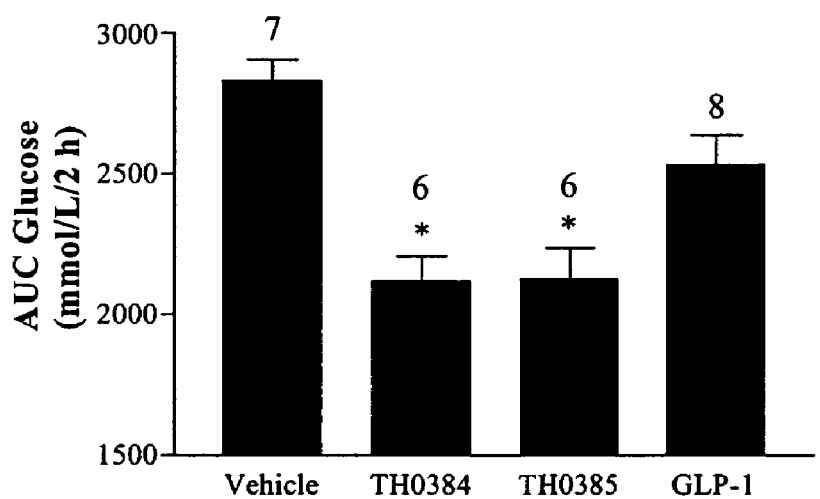
Figure 13:
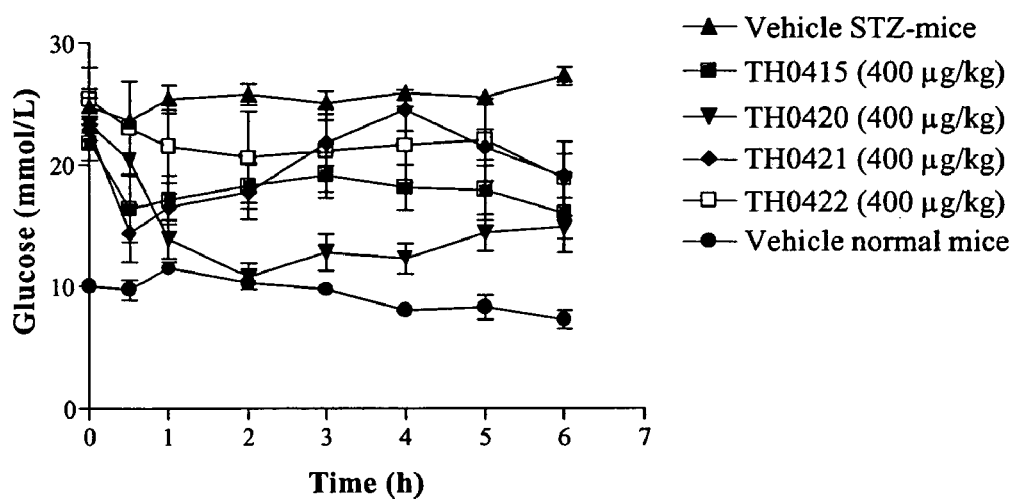
Figure 13:
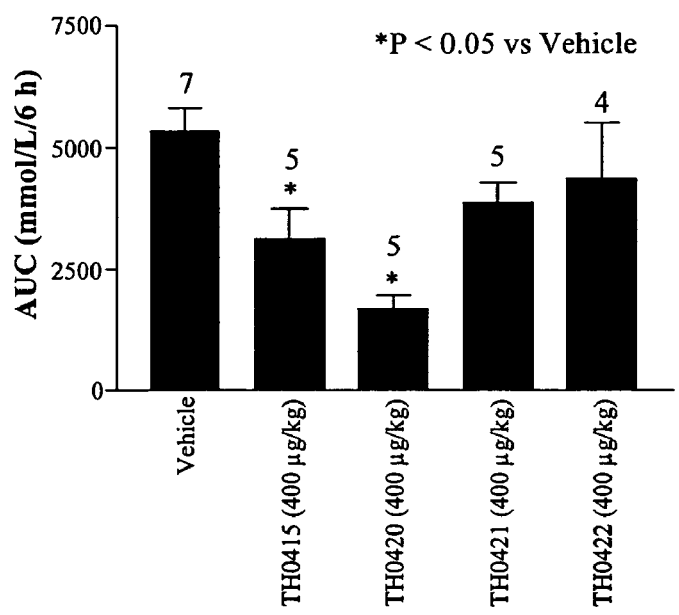
Figure 15:
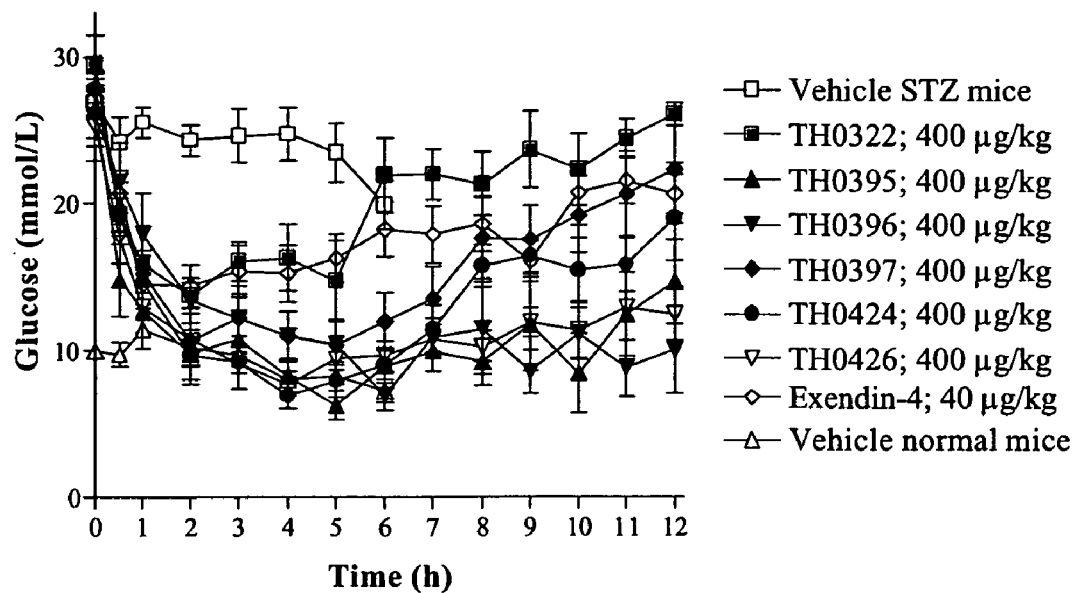
FIG. 15 illustrates the effects of GLP-1 analogs on the glucose profile in fed STZ-induced diabetic CD-1 mice.
Figure 15:
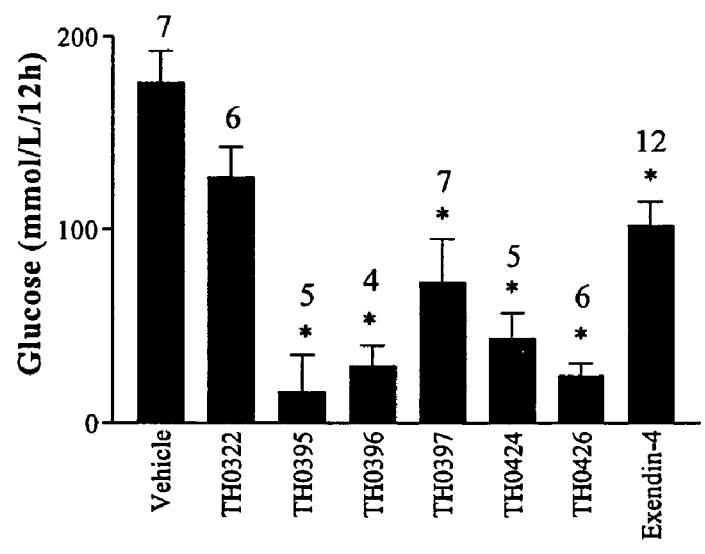

As shown in FIGS. 10 and 15, a similar profile of glucose clearance was found with analogs TH0395, TH0396 and TH0424 in glucose clamped Sprague-Dawley rats and STZ-treated CD-1 mice. These results indicate that the duration of action of TH0395 and TH0396 was longer than that of TH0424.

EXAMPLE 8

Glucose Lowering Effects of GLP-1 Analogs in Fed Streptozotocin-induced Diabetic CD-1 Mice The animals (CD-1 mice) were maintained on standard laboratory chow under a 12:12 light:dark cycle. The animals were kept in groups of 4 mice per cage. The CD-1 mice received an intraperitoneal injection of 400 mg/kg streptozotocin, and 24 hours later received a subcutaneous injection of vehicle or of a selected GLP-1 analogue. The amount of food eaten was monitored for the duration of the experiment. Glucose levels were measured prior to and up to 6-12 hours following the administration of GLP-1 analogue, according to the following time schedule; 0.5, 1, 2, 3, 4, 5, 6, 7, 8, 9, 10, 11 and 12 hours.

A small piece of the tip of the tail of the CD-1 mice was cut with a scalpel and a drop of blood drawn by applying light pressure with the thumb and index from the base of the tail to the tip. The drop of blood was placed on a glucometer strip (Accucheck™ compact, Roche) and a reading obtained. The scab was removed and the same procedure applied for each subsequent measurement.

Figure 14:
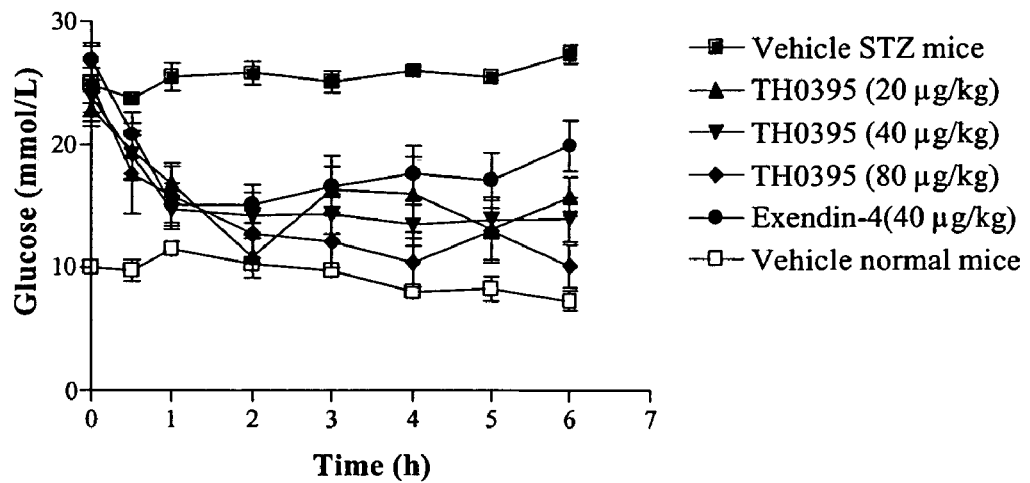
Figure 14:
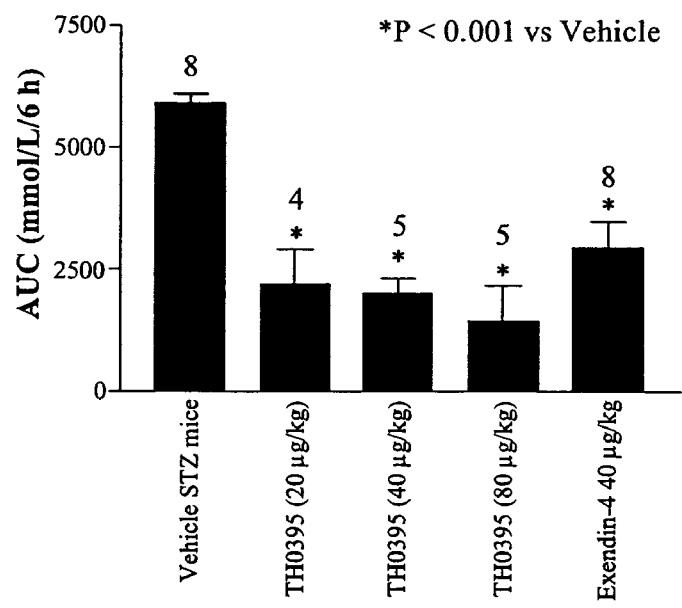
Figure 16:
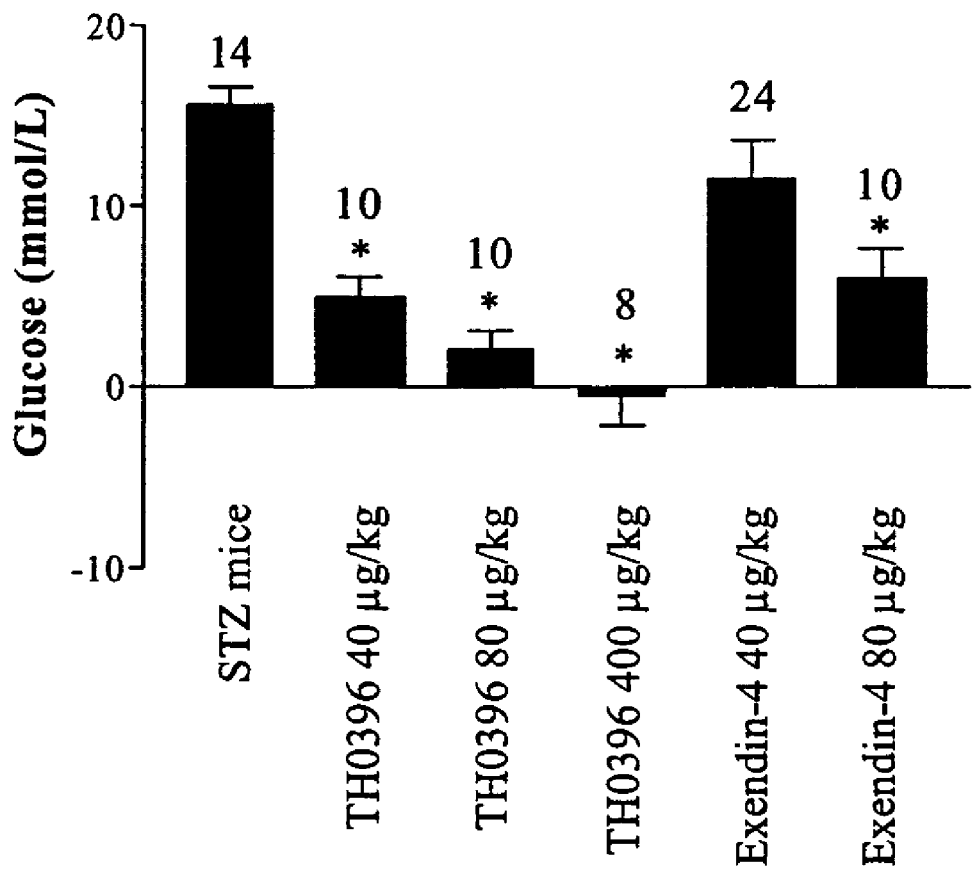
FIG. 16 illustrates a comparison of TH0396 and Exendin-4™ in fed STZ-induced diabetic CD-1 mice at the 12 hour time point. In order to compare the duration of the effects of TH0396 and Exendin-4™, the glucose levels at the last hour of observation were analyzed in a dose-dependent manner. CD-1 mice were treated with streptozotocin and 24 hours later (with a glycemia greater then 20 mmol/L) treated with TH0396 (40, 80 and 400 μg/kg) or Exendin-4™ (40 and 80 μg/kg) and allowed to eat ad libidum for the duration of the experiment (12 hours). At 10:00 am, the animals were injected subcutaneously with the agent. Blood glucose levels were measured for 12 hours post-injection (mean ±SEM; upper panel). Average glucose levels at 11 and 12 hours are presented after subtracting the fed glucose levels of normal mice (n is the number of animals as presented on top of the lower panel bars).
Figure 17:
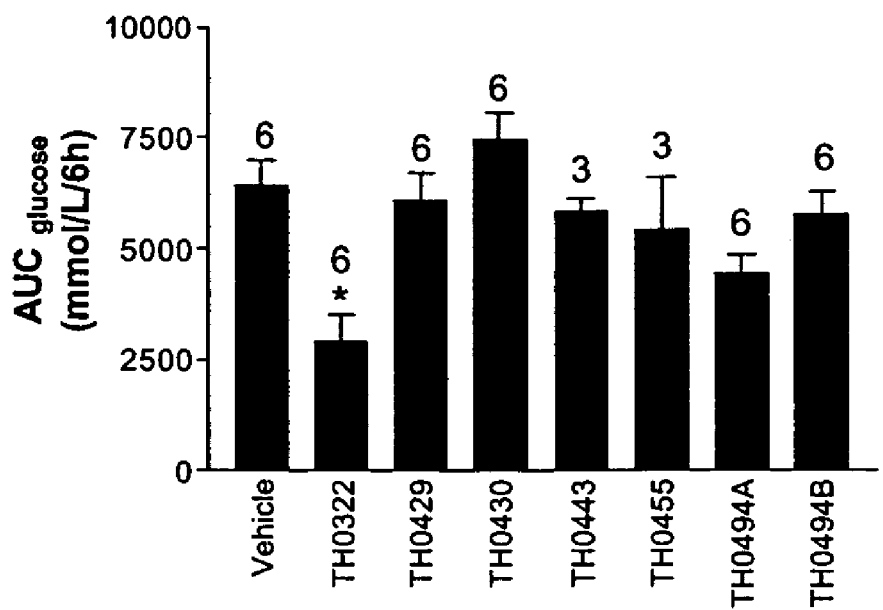
FIG. 17 illustrates the effects of different GLP-1 analogs in STZ-induced diabetic CD-1 mice. Peptides were injected subcutaneously at a dose of 400 μg/kg; n=3 or 6 as indicated on top of bars. Data are mean ±SEM.
Figure 17:
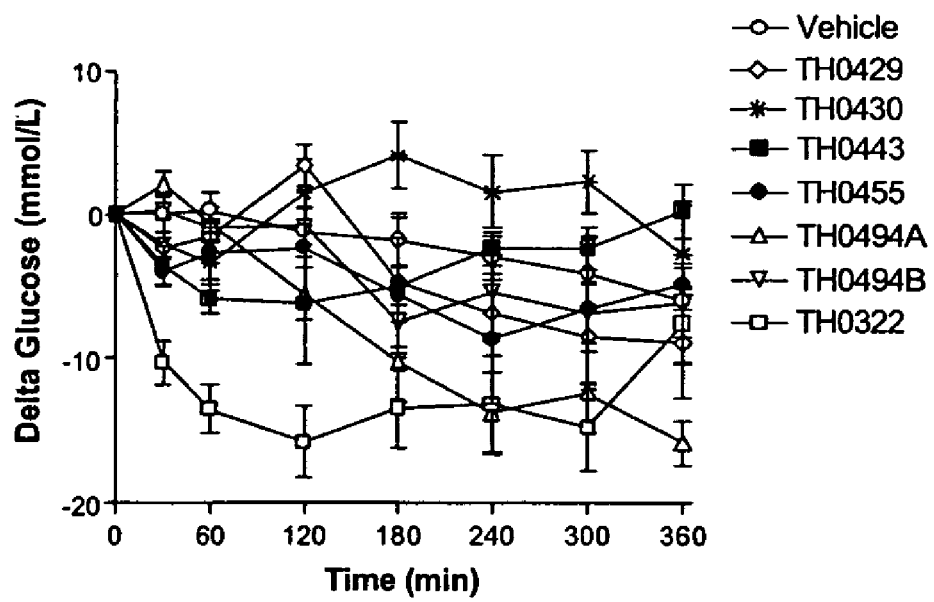
Figure 18:
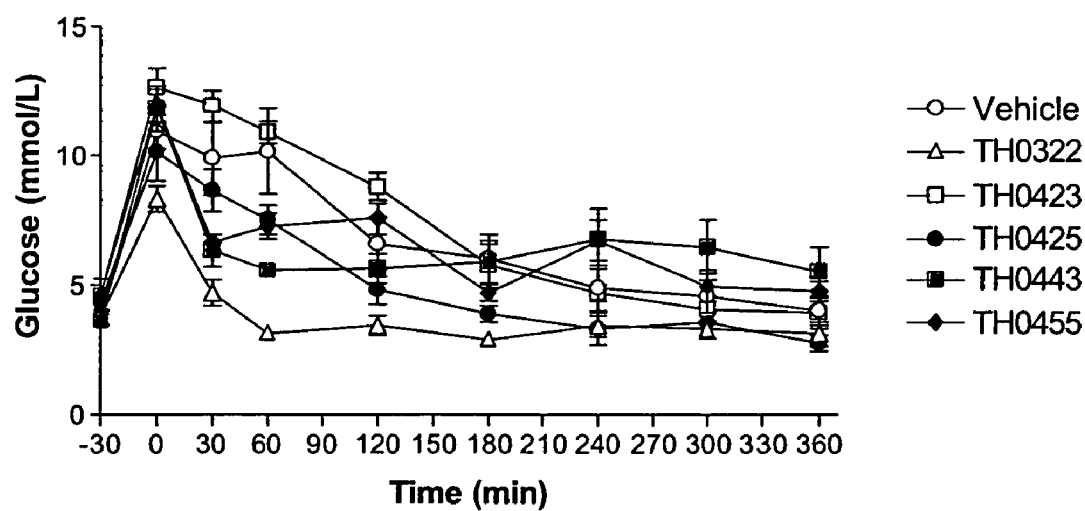
FIG. 18 illustrates the effects of different GLP-1 analogs on post-prandial glycemia in CD-1 mice. Peptides were injected subcutaneously at a dose of 400 μg/kg; n=4-8. Data are mean ±SEM.

As shown in FIGS. 12, 13, 14, 15 and 16, the present study revealed three analogs, TH0395, TH0396 and TH0424 with extended duration of action. These analogs brought the glucose levels of streptozotocin-induced diabetic mice down to those seen in normal feeding mice. It is interesting to note that TH0395 appears to be more potent then Exendin-4™ in STZ-induced diabetic mice, at least for the initial 6 hours of the study (FIG. 14). This is also the case for TH0396 in the initial 12 hours of the study (FIG. 16).

Although the present invention has been described hereinabove by way of preferred embodiments thereof, it can be modified, without departing from the spirit and nature of the subject invention as defined in the appended claims.

What is claimed is:

1. A GLP-1 analog comprising the following sequence:
R1-His-X8-Glu-Gly-Thr-Phe-Thr-Ser-Asp-Val-Ser-Ser-Tyr-X20-Glu-Gly-Gln-Ala-Ala-Lys-X27-Phe-Ile-X30-Trp-Leu-X33 (SEQ ID NOs: 1 to 11, depending on the nature of X33)
wherein:
(i) R1 is 2-hydroxybenzoyl or hydrogen; X8 is Ala or Gly; X20 is selected from the group consisting of Leu and Gly having a $C_6$-$C_{20}$ alkyl side chain; X27 is Ala or Leu; X30 is Glu or Gln, and X33 is Val-Lys-Asn-$NH_2$; or
(ii) R1 is 2-hydroxybenzoyl or hydrogen; X8 is Ala or Gly; X20 is selected from the group consisting of Leu and Gly having a $C_6$-$C_{20}$ alkyl side chain; X27 is Ala or Leu; X30 is Glu; and X33 is Lys-Asn-$NH_2$; or
(iii) R1 is 2-hydroxybenzoyl, trans-3-hexenoyl or hydrogen; X8 is Ala or Gly; X20 is selected from the group consisting of Leu and Gly having a $C_6C_{20}$ alkyl side chain; X27 is Leu; X30 is Glu; and X33 is Lys-Asn-Aib-$NH_2$; or
(iv) R1 is trans-3-hexenoyl or hydrogen; X8 is Ala or Gly; X20 is selected from the group consisting of Leu and Gly having a $C_6$-$C_{20}$ alkyl side chain; X27 is Ala or Leu; X30 is Glu; and X33 is Lys-Asn-$NH_2$; or
(v) R1 is trans-3-hexenoyl or hydrogen; X8 is Ala or Gly; X20 is (S)-Octylglycine; X27 is Ala or Leu; X30 is Glu, Gln or Asp; and X33 is Lys-Asn-$NH_2$ or Val-Lys-Asn-$NH_2$; or
(vi) the GLP-1 analog has a sequence selected from the group consisting of: SEQ ID NO:16, SEQ ID NO:17, SEQ ID NO:18; SEQ ID NO:19; SEQ ID NO: 20; SEQ ID NO: 21; SEQ ID NO: 22; SEQ ID NO: 23; SEQ ID NO:24; SEQ ID NO: 25; SEQ ID NO:26, SEQ ID NO: 27, SEQ ID NO:28, SEQ ID NO: 29; SEQ ID NO: 30, SEQ ID NO: 31, SEQ ID NO: 32; SEQ ID NO: 33; SEQ ID NO: 34; SEQ ID NO: 35, SEQ ID NO:36, AND SEQ ID NO: 38.

2. The GLP-1 analog of claim 1, wherein R1 is 2-hydroxybenzoyl or hydrogen; X8 is Ala or Gly; X27 is Ala or Leu; X30 is Glu or Gln, and X33 is Val-Lys-Asn-$NH_2$.

3. The GLP-1 analog of claim 1, wherein R1 is 2-hydroxybenzoyl or hydrogen; X8 is Ala or Gly; X27 is Ala or Leu; X30 is Glu; and X33 is Lys-Asn-$NH_2$.

4. The GLP-1 analog of claim 1, wherein R1 is 2-hydroxybenzoyl, trans-3-hexenoyl or hydrogen; X8 is Ala or Gly; X27 is Leu; X30 is Glu; and X33 is Lys-Asn-Aib-$NH_2$.

5. The GLP-1 analog of claim 1, wherein R1 is trans-3-hexenoyl or hydrogen; X8 is Ala or Gly; X27 is Ala or Leu; X30 is Glu; and X33 is Lys-Asn-$NH_2$.

6. The GLP-1 analog of claim 1, wherein R1 is trans-3-hexenoyl or hydrogen; X8 is Ala or Gly; X20 is (S)-Octylglycine; X27 is Ala or Leu; X30 is Glu, Gln or Asp; and X33 is Lys-Asn-$NH_2$ or Val-Lys-Asn-$NH_2$.

7. The GLP-1 analog of claim 1, having the following sequence: His-Gly-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Val-Lys-Asn-$NH_2$ (SEQ ID NO: 16).

8. The GLP-1 analog of claim 1, having the following sequence: 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-$NH_2$ (SEQ ID NO: 17).

9. The GLP-1 analog of claim 1, having the following sequence: 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Lys-Asn-Aib-$NH_2$ (SEQ ID NO: 18).

10. The GLP-1 analog of claim 1, having the following sequence: His-Gly-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Lys-Asn-$NH_2$ (SEQ ID NO: 19).

11. The GLP-1 analog of claim 1, having the following sequence: His-Gly-Glu-Gly-Thr-Phe-Thr-Ser-Asp-Val-Ser-Ser-Tyr-[(S)-Octylglycine]-Glu-Gly-Gln-Ala-Ala-Lys-Ala-Phe-Ile-Glu-Trp-Leu-Lys-Asn-$NH_2$ (SEQ ID NO: 20).

12. The GLP-1 analog of claim 1, having the following sequence: trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-$NH_2$ (SEQ ID NO: 21).

13. The GLP-1 analog of claim 1, having the following sequence: trans-3-hexenoyl-NH-His-Ala-Glu-Gly-Thr-Phe- Thr-Ser-Asp-Val-Ser-Ser-Tyr-[(S)-Octylglycine]-Glu-Gly-Gln-Ala-Ala-Lys-Ala-Phe-Ile-Glu-Trp-Leu-Lys-Asn-NH2 (SEQ ID NO: 22).

14. The GLP-1 analog of claim 1, having the following sequence: trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Val-Lys-Asn-NH$_2$ (SEQ ID NO: 23).

15. The GLP-1 analog of claim 1, having the following sequence: trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Lys-Asn-NH$_2$ (SEQ ID NO: 24).

16. The GLP-1 analog of claim 1, having the following sequence: trans-3-hexenoyl-NH-His-Ala-Glu-Gly-Thr-Phe-Thr-Ser-Asp-Val-Ser-Ser-Tyr-Leu-Glu-Gly-Gln-Ala-Ala-Lys-Ala-Phe-Ile-Glu-Trp-Leu-Val-Lys-Asn-NH$_2$ (SEQ ID NO: 25).

17. The GLP-1 analog of claim 1, having the following sequence: trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Ala-Phe-Ile-Glu-Trp-Leu-Val-Lys-Asn-NH$_2$ (SEQ ID NO: 26).

18. The GLP-1 analog of claim 1, having the following sequence: His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Gly-Arg-NH$_2$ (SEQ ID NO: 27).

19. The GLP-1 analog of claim 1, having the following sequence: His-Gly-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Gly-Arg-NH$_2$ (SEQ ID NO: 28).

20. The GLP-1 analog of claim 1, having the following sequence: trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Gly-Arg-NH$_2$ (SEQ ID NO: 29).

21. The GLP-1 analog of claim 1, having the following sequence: trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Glu-Phe-Ile-Ala-Trp-Leu-Val-Lys-Aib-Arg-NH$_2$ (SEQ ID NO: 30).

22. The GLP-1 analog of claim 1, having the following sequence: 2-Hydroxybenzoyl-NH-His-Ala-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-Gly-NH$_2$ (SEQ ID NO: 31).

23. The GLP-1 analog of claim 1, having the following sequence: His-Gly-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Lys-Asn-NH$_2$ (SEQ ID NO: 32).

24. The GLP-1 analog of claim 1, having the following sequence: His-Gly-Glu-Gly-Thr-Phe-Thr-Ser-Asp-Val-Ser-Ser-Tyr-Leu-Glu-Gly-Gln-Ala-Ala-Lys-Leu-Phe-Ile-Glu-Trp-Leu-Val-Lys-Asn-NH$_2$ (SEQ ID NO: 33).

25. The GLP-1 analog of claim 1, having the following sequence: trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Lys-Asn-NH$_2$ (SEQ ID NO: 34).

26. The GLP-1 analog of claim 1, having the following sequence: trans-3-hexenoyl-NH-His-Ala-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Val-Lys-Asn-NH$_2$ (SEQ ID NO: 35).

27. The GLP-1 analog of claim 1, having the following sequence: His-Gly-Glu-Gly-Thr-Phe-Thr-Ser-Asp-Val-Ser-Ser-Tyr-[(S)-Octylglycine]-Glu-Gly-Gln-Ala-Ala-Lys-Leu-Phe-Ile-Glu-Trp-Leu-Lys-Asn-NH$_2$ (SEQ ID NO: 36).

28. The GLP-1 analog of claim 1, having the following sequence: His-Ala-Glu-Gly-Thr-Phe-Thr-Ser-Asp-Val-Ser-Ser-Tyr-[(R)-Octadecylglycine]-Glu-Gly-Gln-Ala-Ala-Lys-Glu-Phe-Ile-Ala-Trp-Leu-Val-Lys-Gly-Arg-NH$_2$ (SEQ ID NO: 38).

29. A pharmaceutical composition comprising one or more pharmaceutically acceptable carriers, diluents, or excipients in combination with a GLP-1 analog according to claim 1, or a pharmaceutically acceptable salt thereof, in an amount effective to reduce serum glucose levels in a diabetic subject.

30. The pharmaceutical composition of claim 29, comprising from about 1 mcg to about 10 mg of the GLP-1 analog or pharmaceutically acceptable salt thereof.

31. A pharmaceutical composition comprising one or more pharmaceutically acceptable carriers, diluents, or excipients in combination with a GLP-1 analog according to claim 1, or a pharmaceutically acceptable salt thereof, in an amount effective to promote production of cAMP from pancreatic beta cells.

32. The pharmaceutical composition of claim 31, comprising from about 1 mcg to about 10 mg of the GLP-1 analog or pharmaceutically acceptable salt thereof.

* * * * *

UNITED STATES PATENT AND TRADEMARK OFFICE
CERTIFICATE OF CORRECTION

PATENT NO.        : 7,538,185 B2
APPLICATION NO.   : 11/031851
DATED             : May 26, 2009
INVENTOR(S)       : Krishna Peri et al.

It is certified that error appears in the above-identified patent and that said Letters Patent is hereby corrected as shown below:

In title page, item (56) References Cited - U.S. Patent Documents, insert
--5,118,666  6/1992  Habener ............ 514/12--.

In claim 1, column 43, line 44, delete "$C_6C_{20}$" and insert --$C_6$-$C_{20}$-- therefor.

Signed and Sealed this

Eleventh Day of August, 2009

David J. Kappos
*Director of the United States Patent and Trademark Office*